US009933434B2

(12) United States Patent
Kipps et al.

(10) Patent No.: US 9,933,434 B2
(45) Date of Patent: Apr. 3, 2018

(54) THERAPEUTIC ANTIBODIES AGAINST ROR-1 PROTEIN AND METHODS FOR USE OF SAME

(71) Applicant: The Regents of the University of California, Oakland, CA (US)

(72) Inventors: Thomas J. Kipps, San Diego, CA (US); George F. Widhopf, II, San Diego, CA (US); Bing Cui, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/346,967

(22) Filed: Nov. 9, 2016

(65) Prior Publication Data

US 2017/0248585 A1    Aug. 31, 2017

Related U.S. Application Data

(63) Continuation of application No. 14/846,400, filed on Sep. 4, 2015, now Pat. No. 9,523,695, which is a continuation of application No. 13/997,934, filed as application No. PCT/US2012/021339 on Jan. 13, 2012, now Pat. No. 9,217,040.

(60) Provisional application No. 61/433,043, filed on Jan. 14, 2011.

(51) Int. Cl.
*G01N 33/68* (2006.01)
*C07K 16/40* (2006.01)
*C07K 16/28* (2006.01)
*A61K 39/00* (2006.01)

(52) U.S. Cl.
CPC ..... *G01N 33/6854* (2013.01); *C07K 16/2803* (2013.01); *C07K 16/40* (2013.01); *A61K 2039/505* (2013.01); *C07K 2317/565* (2013.01); *C07K 2317/73* (2013.01); *C07K 2317/77* (2013.01); *C07K 2317/92* (2013.01)

(58) Field of Classification Search
CPC ............... G01N 33/6854; C07K 16/40; C07K 16/2803; C07K 2317/92
See application file for complete search history.

(56) References Cited

U.S. PATENT DOCUMENTS

| | | |
|---|---|---|
| 5,455,030 A | 10/1995 | Ladner et al. |
| 5,591,593 A | 1/1997 | Courtenay-Luck |
| 5,639,641 A | 6/1997 | Pedersen et al. |
| 5,776,456 A | 7/1998 | Anderson et al. |
| 5,783,184 A | 7/1998 | Appelbaum et al. |
| 5,830,470 A | 11/1998 | Nakamura et al. |
| 5,830,663 A | 11/1998 | Embleton et al. |
| 5,837,243 A | 11/1998 | Deo et al. |
| 5,843,749 A | 12/1998 | Maisonpierre et al. |
| 5,861,155 A | 1/1999 | Lin |
| 5,969,107 A | 10/1999 | Carceller et al. |
| 5,977,316 A | 11/1999 | Chatterjee et al. |
| 6,080,588 A | 6/2000 | Glick |
| 6,291,208 B1 | 9/2001 | Anand et al. |
| 6,309,636 B1 | 10/2001 | do Couto et al. |
| 6,323,027 B1 | 11/2001 | Burkly et al. |
| 6,559,294 B1 | 5/2003 | Griffais et al. |
| 6,562,958 B1 | 5/2003 | Breton et al. |
| 6,586,251 B2 | 7/2003 | Economides et al. |
| 6,596,541 B2 | 7/2003 | Murphy et al. |
| 6,699,703 B1 | 3/2004 | Doucette-Stamm et al. |
| 6,703,491 B1 | 3/2004 | Homburger et al. |
| 6,753,314 B1 | 6/2004 | Giot et al. |
| 6,764,851 B2 | 7/2004 | Nikolau et al. |
| 6,800,744 B1 | 10/2004 | Doucette-Stamm et al. |
| 6,806,079 B1 | 10/2004 | McCafferty et al. |
| 6,812,339 B1 | 11/2004 | Venter et al. |
| 6,815,540 B1 | 11/2004 | Pluckthun et al. |
| 6,822,071 B1 | 11/2004 | Stephens et al. |
| 6,825,325 B1 | 11/2004 | Fischer et al. |
| 6,833,446 B1 | 12/2004 | Wood et al. |
| 6,833,447 B1 | 12/2004 | Goldman et al. |
| 6,881,557 B2 | 4/2005 | Foote |
| 6,897,044 B1 | 5/2005 | Braslawsky et al. |
| 6,919,183 B2 | 7/2005 | Fandl et al. |
| 6,942,984 B2 | 9/2005 | Bertin |
| 6,979,446 B2 | 12/2005 | Patti et al. |
| 7,034,121 B2 | 4/2006 | Carreno et al. |
| 7,041,490 B1 | 5/2006 | Griffais et al. |
| 7,105,348 B2 | 9/2006 | Murphy et al. |
| 7,138,272 B1 | 11/2006 | Cichutek et al. |

(Continued)

FOREIGN PATENT DOCUMENTS

| | | |
|---|---|---|
| CN | 103792364 A | 5/2014 |
| EP | 0 332 424 A2 | 9/1989 |

(Continued)

OTHER PUBLICATIONS

Baskar, S. et al. (Jan. 15, 2008). "Unique cell surface expression of receptor tyrosine kinase ROR1 in human B-cell chronic lymphocytic leukemia," *Clin Cancer Res* 14(2):396-404.

Brown, M. et al. (May 1996). "Tolerance of single, but not multiple, amino acid replacements in antibody VH CDR 2: a means of minimizing B cell wastage from somatic hypermutation?" *J. Immunology* 156(9):3285-3291.

(Continued)

*Primary Examiner* — Ruixiang Li

(74) *Attorney, Agent, or Firm* — Mintz Levin Cohn Ferris Glovsky and Popeo, P.C.

(57) ABSTRACT

Therapeutic antibodies having binding specificity for ROR-1 expressed on cancer cells (particularly leukemic and lymphomic cells) and pharmaceutical compositions containing one or more such antibodies for use in treating cancer. Methods for diagnosing such cancers through in vitro detection of binding to ROR-1 protein expressed on putative cancer cells are also provided.

11 Claims, 25 Drawing Sheets

(56) References Cited

U.S. PATENT DOCUMENTS

| | | |
|---|---|---|
| 7,151,164 B2 | 12/2006 | Hausen et al. |
| 7,157,238 B2 | 1/2007 | Schmitt et al. |
| 7,205,450 B2 | 4/2007 | Cook et al. |
| 7,232,888 B2 | 6/2007 | Begent et al. |
| 7,282,336 B2 | 10/2007 | Wallace et al. |
| 7,294,753 B2 | 11/2007 | Kloetzer et al. |
| 7,297,341 B1 | 11/2007 | Murdin et al. |
| 7,317,091 B2 | 1/2008 | Lazar et al. |
| 7,319,139 B2 | 1/2008 | Braslawsky et al. |
| 7,319,142 B1 | 1/2008 | Goldman et al. |
| 7,332,162 B1 | 2/2008 | Deckmyn et al. |
| 7,361,478 B2 | 4/2008 | Adorante et al. |
| 7,408,041 B2 | 8/2008 | Bowdish et al. |
| 7,435,553 B2 | 10/2008 | Fandl et al. |
| 7,435,804 B2 | 10/2008 | Kordyum et al. |
| 7,462,698 B2 | 12/2008 | Aoyagi et al. |
| 7,468,472 B2 | 12/2008 | Cahoon et al. |
| 7,534,604 B2 | 5/2009 | Fandl et al. |
| 7,538,206 B2 | 5/2009 | Cole |
| 7,557,191 B2 | 7/2009 | Abrahamson et al. |
| 7,589,257 B2 | 9/2009 | Hershey et al. |
| 7,608,700 B2 | 10/2009 | Klaenhammer et al. |
| 7,612,181 B2 | 11/2009 | Wu et al. |
| 7,629,444 B1 | 12/2009 | Goldman et al. |
| 7,649,083 B2 | 1/2010 | Winston, Jr. et al. |
| 7,662,379 B2 | 2/2010 | Presta |
| 7,674,459 B2 | 3/2010 | Fung et al. |
| 7,691,977 B2 | 4/2010 | Fuh et al. |
| 7,722,876 B2 | 5/2010 | Polonelli et al. |
| 7,723,110 B2 | 5/2010 | Chang et al. |
| 7,727,525 B2 | 6/2010 | Wu et al. |
| 7,740,847 B2 | 6/2010 | Allan et al. |
| 7,744,874 B2 | 6/2010 | Korytko et al. |
| 7,754,208 B2 | 7/2010 | Ledbetter et al. |
| 7,754,209 B2 | 7/2010 | Ledbetter et al. |
| 7,807,154 B2 | 10/2010 | Strasburger et al. |
| 7,807,794 B2 | 10/2010 | Lazarides et al. |
| 7,820,165 B2 | 10/2010 | McKenna et al. |
| 7,820,166 B2 | 10/2010 | Lanzavecchia |
| 7,829,086 B2 | 11/2010 | Hilbert et al. |
| 7,834,154 B2 | 11/2010 | Koch et al. |
| 7,887,805 B2 | 2/2011 | Pedersen et al. |
| 7,910,702 B2 | 3/2011 | Kav et al. |
| 7,915,387 B2 | 3/2011 | Durrant et al. |
| 7,915,388 B2 | 3/2011 | Wu et al. |
| 7,919,273 B2 | 4/2011 | Goldenberg et al. |
| 7,935,791 B2 | 5/2011 | Fung et al. |
| 7,939,087 B2 | 5/2011 | Telford et al. |
| 7,959,915 B2 | 6/2011 | Jay et al. |
| 7,959,916 B2 | 6/2011 | Spies et al. |
| 7,968,686 B2 | 6/2011 | Korytko et al. |
| 7,977,067 B2 | 7/2011 | Power et al. |
| 7,977,457 B2 | 7/2011 | Reiter et al. |
| 8,025,878 B2 | 9/2011 | Gellerfors et al. |
| 8,075,884 B2 | 12/2011 | Bowdish et al. |
| 8,101,726 B2 | 1/2012 | Parry et al. |
| 8,110,369 B2 | 2/2012 | Rump et al. |
| 8,119,385 B2 | 2/2012 | Mathur et al. |
| 8,124,079 B2 | 2/2012 | Goetsch et al. |
| 8,124,380 B2 | 2/2012 | Phalipon et al. |
| 8,147,832 B2 | 4/2012 | Carr et al. |
| 8,153,134 B2 | 4/2012 | Bigler et al. |
| 8,163,283 B2 | 4/2012 | Lee |
| 8,168,427 B2 | 5/2012 | Sahin et al. |
| 8,192,740 B2 | 6/2012 | Kimura |
| 8,212,009 B2 | 7/2012 | Kipps et al. |
| 8,221,754 B2 | 7/2012 | Kanayama et al. |
| 8,222,376 B2 | 7/2012 | Padkær et al. |
| 8,231,875 B2 | 7/2012 | Adams et al. |
| 8,236,315 B2 | 8/2012 | Lazarides et al. |
| 8,252,287 B2 | 8/2012 | Takeyama et al. |
| 8,258,263 B2 | 9/2012 | Morrison et al. |
| 8,263,743 B2 | 9/2012 | Smith et al. |
| 8,287,865 B2 | 10/2012 | Hansen et al. |
| 8,298,531 B2 | 10/2012 | Mottl |
| 8,298,532 B2 | 10/2012 | Fandl et al. |
| 8,301,398 B2 | 10/2012 | Garrett et al. |
| 8,309,323 B2 | 11/2012 | Martin et al. |
| 8,343,489 B2 | 1/2013 | Weaver et al. |
| 8,344,112 B2 | 1/2013 | Goetsch et al. |
| 8,344,211 B2 | 1/2013 | Alexandrov et al. |
| 8,357,782 B2 | 1/2013 | Fukuda et al. |
| 8,377,443 B2 | 2/2013 | McCauley et al. |
| 8,383,778 B2 | 2/2013 | Hsieh et al. |
| 8,394,379 B2 | 3/2013 | Imboden et al. |
| 8,394,926 B2 | 3/2013 | Lutterbuse et al. |
| 8,409,577 B2 | 4/2013 | Thompson et al. |
| 8,468,130 B2 | 6/2013 | Bhandari et al. |
| 8,470,324 B2 | 6/2013 | Fandl et al. |
| 8,486,398 B2 | 7/2013 | Van Ryn et al. |
| 8,507,222 B2 | 8/2013 | Wong et al. |
| 8,519,225 B2 | 8/2013 | Boukharov et al. |
| 8,586,714 B2 | 11/2013 | Ghayur et al. |
| 8,597,898 B2 | 12/2013 | Fandl et al. |
| 8,633,139 B2 | 1/2014 | DuBridge et al. |
| 8,658,175 B2 | 2/2014 | Dubridge et al. |
| 8,691,224 B2 | 4/2014 | Barghorn et al. |
| 8,703,427 B2 | 4/2014 | Deonarain et al. |
| 8,710,022 B2 | 4/2014 | Takahashi et al. |
| 8,728,803 B2 | 5/2014 | Thompson et al. |
| 8,735,553 B1 | 5/2014 | Li et al. |
| 8,753,631 B2 | 6/2014 | Karpatkin et al. |
| 8,759,009 B2 | 6/2014 | Lazarides et al. |
| 8,759,105 B2 | 6/2014 | Economides et al. |
| 8,759,494 B2 | 6/2014 | Bachmann et al. |
| 8,815,242 B2 | 8/2014 | Harvey |
| 8,821,871 B2 | 9/2014 | Van Ryn et al. |
| 8,822,645 B2 | 9/2014 | Ghayur et al. |
| 8,828,398 B2 | 9/2014 | Kobayashi et al. |
| 8,835,610 B2 | 9/2014 | Hsieh et al. |
| 8,846,402 B2 | 9/2014 | Economides et al. |
| 8,852,593 B2 | 10/2014 | Baurin et al. |
| 8,853,365 B2 | 10/2014 | Wu et al. |
| 8,858,949 B2 | 10/2014 | Yokoseki et al. |
| 8,859,501 B2 | 10/2014 | Nordstrom et al. |
| 8,865,430 B2 | 10/2014 | Fandl et al. |
| 8,871,908 B2 | 10/2014 | Liu et al. |
| 8,877,686 B2 | 11/2014 | Zha et al. |
| 8,916,152 B2 | 12/2014 | Hernandez Miguez et al. |
| 8,927,233 B2 | 1/2015 | Fandl et al. |
| 8,933,197 B2 | 1/2015 | Stemmer et al. |
| 8,940,303 B2 | 1/2015 | Kirby et al. |
| 8,945,543 B2 | 2/2015 | Igawa et al. |
| 8,951,532 B2 | 2/2015 | Mermer et al. |
| 8,952,217 B2 | 2/2015 | Puzio et al. |
| 8,975,376 B2 | 3/2015 | Blein et al. |
| 8,980,267 B2 | 3/2015 | Grewal et al. |
| 8,993,524 B2 | 3/2015 | Bedi et al. |
| 9,011,852 B2 | 4/2015 | Rother et al. |
| 9,017,684 B2 | 4/2015 | Aburatani et al. |
| 9,018,445 B2 | 4/2015 | Vinocur et al. |
| 9,023,995 B2 | 5/2015 | Brown et al. |
| 9,034,322 B2 | 5/2015 | Fischetti et al. |
| 9,035,027 B2 | 5/2015 | Ghayur et al. |
| 9,045,541 B2 | 6/2015 | Eckelman et al. |
| 9,045,543 B2 | 6/2015 | Liu et al. |
| 9,056,911 B2 | 6/2015 | Yang et al. |
| 9,068,204 B2 | 6/2015 | Donovan et al. |
| 9,085,623 B2 | 7/2015 | Rother et al. |
| 9,090,686 B2 | 7/2015 | Klinguer-Hamour |
| 9,090,889 B2 | 7/2015 | Nunn, Jr. et al. |
| 9,102,724 B2 | 8/2015 | Cummings et al. |
| 9,150,647 B2 | 10/2015 | Mellstedt et al. |
| 9,163,258 B2 | 10/2015 | Riddell et al. |
| 9,217,040 B2 | 12/2015 | Kipps et al. |
| 9,228,023 B2 | 1/2016 | Rohlff et al. |
| 9,228,208 B2 | 1/2016 | Frendewey et al. |
| 9,242,014 B2 | 1/2016 | Kipps et al. |
| 9,266,952 B2 | 2/2016 | Teige |
| 9,316,646 B2 | 4/2016 | Rader et al. |
| 9,523,695 B2 | 12/2016 | Kipps et al. |
| 2009/0137416 A1 | 5/2009 | Fandl et al. |
| 2010/0040616 A1 | 2/2010 | Leung et al. |
| 2010/0062005 A1 | 3/2010 | Kipps et al. |

(56) References Cited

U.S. PATENT DOCUMENTS

| | | |
|---|---|---|
| 2010/0129817 A1 | 5/2010 | Wei et al. |
| 2011/0165650 A1 | 7/2011 | Fandl et al. |
| 2012/0052007 A1 | 3/2012 | Trieu et al. |
| 2012/0282177 A1 | 11/2012 | Rohlff et al. |
| 2013/0302346 A1 | 11/2013 | Brommage, Jr. et al. |
| 2014/0072979 A1 | 3/2014 | Fandl et al. |
| 2014/0072980 A1 | 3/2014 | Fandl et al. |
| 2014/0134719 A1 | 5/2014 | Despande et al. |
| 2014/0170134 A1 | 6/2014 | Schneewind et al. |
| 2014/0272931 A1 | 9/2014 | Ziemann et al. |
| 2014/0316186 A1 | 10/2014 | Hallahan et al. |

FOREIGN PATENT DOCUMENTS

| | | |
|---|---|---|
| EP | 0 332 424 A3 | 9/1989 |
| EP | 233.8 486 A2 | 5/1990 |
| EP | 233.8 486 A3 | 5/1990 |
| EP | 2 617 320 A1 | 7/2013 |
| KR | 2003-0024004 A | 3/2003 |
| WO | WO-2007/109747 A2 | 9/2007 |
| WO | WO-2007/109747 A3 | 9/2007 |
| WO | WO-2007/146957 A2 | 12/2007 |
| WO | WO-2007/146957 A3 | 12/2007 |
| WO | WO-2008/076868 A2 | 6/2008 |
| WO | WO-2008/076868 A3 | 6/2008 |
| WO | WO-2008/103849 A2 | 8/2008 |
| WO | WO-2008/103849 A3 | 8/2008 |
| WO | WO-2008/103849 A4 | 8/2008 |
| WO | WO-2010/008069 A1 | 1/2010 |
| WO | WO-2010/017468 A1 | 2/2010 |
| WO | WO-2010/124188 A1 | 10/2010 |
| WO | WO-2011/054007 A1 | 5/2011 |
| WO | WO-2011/079902 A2 | 7/2011 |
| WO | WO-2011/079902 A3 | 7/2011 |
| WO | WO-2011/137114 A1 | 11/2011 |
| WO | WO-2011/153431 A2 | 12/2011 |
| WO | WO-2011/153431 A3 | 12/2011 |
| WO | WO-2011/159847 A2 | 12/2011 |
| WO | WO-2011/159847 A3 | 12/2011 |
| WO | WO-2012/076066 A1 | 6/2012 |
| WO | WO-2012/076727 A1 | 6/2012 |
| WO | WO-2012/097313 A2 | 7/2012 |
| WO | WO-2012/097313 A3 | 7/2012 |
| WO | WO-2013/025834 A2 | 2/2013 |
| WO | WO-2013/025834 A3 | 2/2013 |
| WO | WO-2013/025834 A9 | 2/2013 |
| WO | WO-2013/078377 A1 | 5/2013 |
| WO | WO-2013/078377 A9 | 5/2013 |
| WO | WO-2014/141064 A1 | 9/2014 |
| WO | WO-2014/143343 A1 | 9/2014 |
| WO | WO-2014/143343 A8 | 9/2014 |
| WO | WO-2014/167022 A1 | 10/2014 |
| WO | WO-2015/089502 A2 | 6/2015 |
| WO | WO-2015/089502 A3 | 6/2015 |
| WO | WO-2016/000619 A1 | 1/2016 |
| WO | WO-2016/007775 A1 | 1/2016 |

OTHER PUBLICATIONS

Choudhury, A. et al. (Nov. 2010, e-published Aug. 31, 2010). "Silencing of ROR1 and FMOD with siRNA Results in Apoptosis of CLL Cells," *Br. J. Haematol.* 151(4):327-335.

Daneshmanesh, A.H. et al. (Sep. 1, 2008). "Roil, a Cell Surface Receptor Tyrosine Kinase is Expressed in Chronic Lymphocytic Leukemia and May Serve as a Putative Target for Therapy," *Int. J. Cancer* 123(5):1190-1195.

Extended European Search Report Regarding EP 12 734 733.4.

Fukuda, T. et al. (Feb. 26, 2008, e-published Feb. 19, 2008). "Antisera induced by infusions of autologous Ad-CD154-leukemia B cells identify ROR1 as an oncofetal antigen and receptor for Wnt5a," *Proc Natl Acad Sci USA* 105(8):3047-3052.

Paul, William, Fundamental Immunology, 3rd Edition, Raven Press, New York, 1993, pp. 292-295.

Rudikoff, S. et al. (Mar. 1982). "Single amino acid substitution altering antigen-binding specificity," *Proc. Natl. Acad. Sci. USA* 79(6):1979-1983.

Vajdos, F.F. et al. (Jul. 5, 2002). "Comprehensive functional maps of the antigen-binding site of an anti-ErbB2 antibody obtained with shotgun scanning mutagenesis," *J. Mol. Biol.* 320(2):415-428.

Yang et al., "Therapeutic Potential and Challenges of Targeting Receptor Tyrosine Kinase ROR1 with Monoclonal Antibodies in B-Cell Malignancies," *PLoS One* (2011), 6(6):e21018, 1-14, Blackwell Science Ltd.

Human and Murine ROR1 Proteins are Highly Conserved

| Region | Position | # of different aa |
|---|---|---|
| Ig-like | 1–147aa | 12 |
| Linker between Ig-like and CRD | 148–165aa | 1 |
| CRD | 166–299aa | 1 |
| Linker between CRD and Kringle | 300–312aa | 0 |
| Kringle | 313–391aa | 1 |
| Linker between Kringle and TM | 392–406aa | 0 |

Domain Structure and Sequence Homology of Human and Murine ROR1 Extracellular Protein

```
hROR1  MHRPRRRGTRPPLLALLAALLLAARGAAAQETELSVSAELVPTSSWNISSELNKDSYLILDEPMNNITTSLGQTAELHCK  80
mROR1  ..........P.................D............T...ID.G.............................

Ig Domain
hROR1  VSGNPPPTIRWFKNDAPVVQEPRRLSPRSTIYGSRLRIRNLDTTDTGYFQCVATNGKEVVSSTGVLFVKFGPPPTASPGY  160
mROR1  .....S..................I..A.N..............................K...T............S Cysteine Rich Domain
hROR1  SDEYEEDGFCQPYRGIACARFIGNRTVYMESLHMQGEIENQITAAFTMIGTSSHLSDKCSQFAIPSLCHYAFPYCDETSS  240
mROR1  ...............................................................................

hROR1  VPKPRDLCRDECEILENVLCQTEYIFARSNPMILMRLKLPNCEDLPQPESPEAANCIRIGIPMADPINKNHKCYNSTGVD  320
mROR1  ....................V..........................................................

Kringle
hROR1  YRGTVSVTKSGROCQPWNSQYPHTHTFTALRFPELNWGGHSYCRNPGNQKEAPWCFTLDENFKSDLCDIPACDSKDSKEKN  400
mROR1  ..................S............................................................

hROR1  KMEILY
mROR1  X.....
```

FIG. 11

Anti-RORI Mabs Generated Across Extracellular Domain

| No. | Binding sites of antibodies | | | | |
|---|---|---|---|---|---|
| | 5'-Ig-like | Middle of Ig-like | 3'-Ig-like | CRD | Kringle |
| 1-4A5 | | ✓ | | | |
| G11 | | ✓ | | | |
| H11 | | ✓ | | | |
| 2G3 | | ✓ | | | |
| 3-D10 | | | ✓ | | |

FIG. 12

3-D10 Kd Determination

Analysis(x)

Baseline / Endpoints:
5 to 10 [sec] from beginning
10 to 5 [sec] from end

| Ignore | Binding Signal (V) | Concentration |
|---|---|---|
|  | 0.0499 | 500nM |
|  | 0.0805 | 250nM |
|  | 0.1525 | 125nM |
|  | 0.2084 | 62.5nM |
|  | 0.2405 | 31.25nM |
|  | 0.4173 | 15.63nM |
|  | 0.4760 | 7.81nM |
|  | 0.5175 | 3.90nM |
|  | 0.5015 | 1.95nM |
|  | 0.5390 | 976.56pM |
|  | 0.5496 | 488.28pM |
|  | 0.5581 | 0 |
| ✓ | 0.0012 | 0 |
|  | 0.0082 | 500nM |
|  | 0.0777 | 250nM |
| ✓ | 0.1245 | 125nM |
| ✓ | 0.1684 | 62.5nM |
|  | 0.2908 | 31.25nM |
|  | 0.3642 | 15.63nM |
|  | 0.4170 | 7.81nM |
|  | 0.4595 | 3.90nM |
|  | 0.4782 | 1.95nM |
|  | 0.4804 | 976.56pM |
|  | 0.4870 | 488.28pM |
|  | 0.4968 | 0 |
| ✓ | 0.0049 | 0 |

Kd       = 40.47nM
ABC      = 40.47pM
Ratio    = 0.0010
Sig 100% = 0.54
   Drift = 0.7514
   (%/run)
NSB      = 0.00
   Drift = -0.7086
   (mV/run)
%Error   = 0.82

Kd       = 40.47nM
95% confidence interval
Kd High  = 43.50nM
Kd Low   = 26.25nM ABC      = 40.47pM
95% confidence interval
ABC High = 0.70nM
ABC Low  = Less than 146.19fM

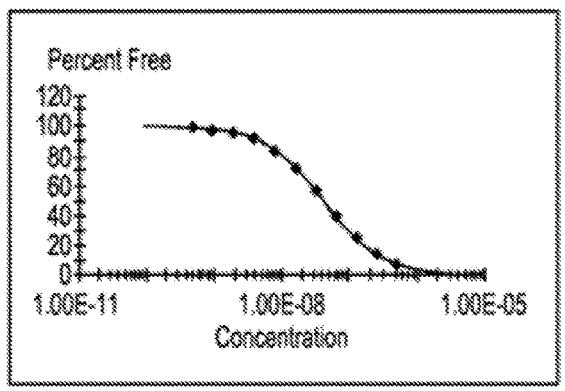

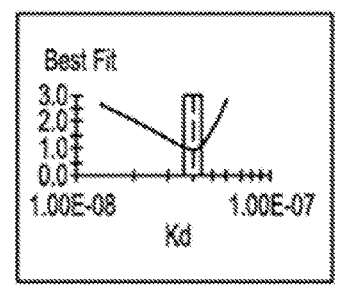

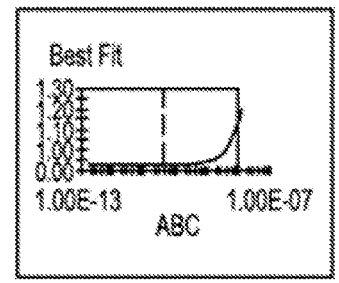

FIG. 16A

1-4A5 Kd Determination

Analysis(x)

Baseline / Endpoints:
0 to 10 [sec] from beginning
10 to 5 [sec] from end

| Ignore | Binding Signal (V) | Concentration |
|---|---|---|
| | 0.0781 | 100nM |
| | 0.0990 | 50nM |
| | 0.1213 | 25nM |
| | 0.1554 | 12.5nM |
| | 0.2060 | 6.25nM |
| | 0.2768 | 3.13nM |
| | 0.3167 | 1.56nM |
| | 0.3613 | 781.25pM |
| | 0.3702 | 390.63pM |
| | 0.3790 | 195.31pM |
| | 0.3895 | 97.66pM |
| | 0.4102 | 48.83pM |
| | 0.3928 | 0 |
| | 0.0616 | 100nM |
| | 0.0646 | 50nM |
| | 0.0995 | 25nM |
| | 0.1257 | 12.5nM |
| | 0.1807 | 6.25nM |
| | 0.2415 | 3.13nM |
| | 0.2903 | 1.56nM |
| | 0.3300 | 781.25pM |
| | 0.3533 | 390.63pM |
| | 0.3650 | 195.31pM |
| | 0.3636 | 97.66pM |
| | 0.3882 | 48.83pM |
| | 0.3758 | 0 |

Kd = 4.53nM
ABC = 62.92pM
Ratio = 0.0139
Sig 100% = 0.40
Drift = -0.0110 (%/run)
NSB = 0.04
Drift = -2.0021 (mV/run)
%Error = 1.53

Kd = 4.53nM
95% confidence interval
Kd High = 5.09nM
Kd Low = 3.33nM

ABC = 62.92pM
95% confidence interval
ABC High = 2.59nM
ABC Low = Less than 227.30fM

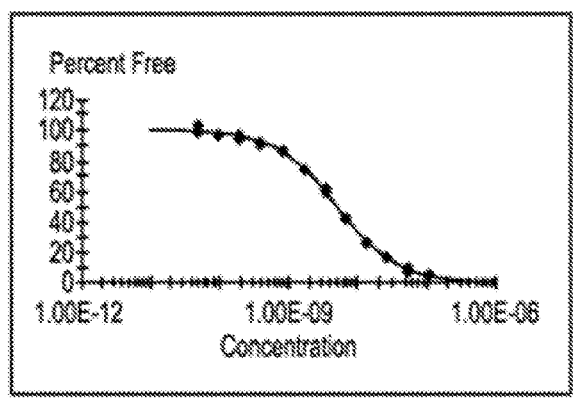

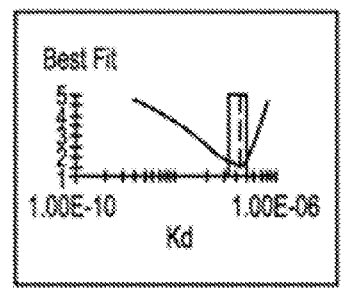

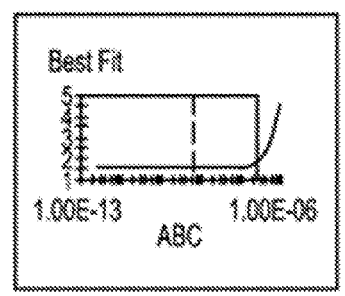

FIG. 16B

3-D10 Anti-ROR1 mAb is Highly Active in *in vivo* Assays

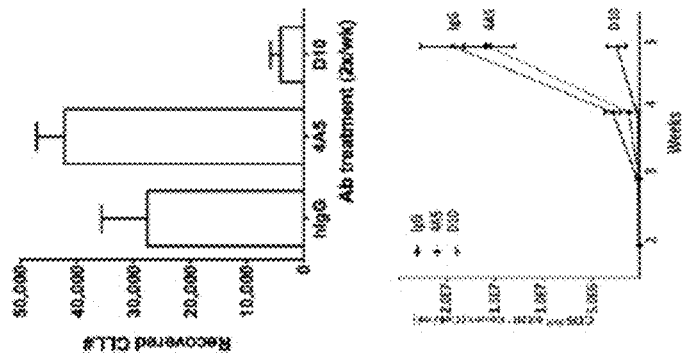

- 3-D10 Mab highly active in *in vivo* niche dependent activity model
  - Substantial reduction in leukemic burden using 4 primary CLL patient products tested in 76 mice
  - Activity much greater than other anti-ROR1 Mabs (4A5)

- 3-D10 Mab active in *in vivo* immune competent mouse model
  - Substantial reduction in spontaneous human ROR1 expressing leukemia model
  - Activity much greater than other anti-ROR1 Mabs (4A5)

3-D10 Mab has greatest anti-ROR1 activity in *in vivo* assay systems

FIG. 17

THERAPEUTIC ANTIBODIES AGAINST ROR-1 PROTEIN AND METHODS FOR USE OF SAME

CROSS-REFERENCES TO RELATED APPLICATIONS

This application is a continuation of U.S. patent application Ser. No. 14/846,400, filed Sep. 4, 2015, which is a continuation of U.S. patent application Ser. No. 13/997,934, filed Jun. 27, 2013, now issued as U.S. Pat. No. 9,217,040, which is a national stage entry of International Patent Application No. PCT/US2012/021339, filed Jan. 13, 2012, which claims the benefit of U.S. Provisional Patent Application No. 61/433,043, filed Jan. 14, 2011, each of which is incorporated herein by reference in its entirety and for all purposes.

STATEMENT AS TO RIGHTS TO INVENTIONS MADE UNDER FEDERALLY SPONSORED RESEARCH AND DEVELOPMENT

This invention was made with government support under NIH CA081534 awarded by The National Institutes of Health. The government has certain rights in the invention.

BACKGROUND

Tyrosine kinases are important mediators of the signaling cascade, determining key roles in diverse biological processes like growth, differentiation, metabolism and apoptosis in response to external and internal stimuli. Studies have implicated the role of tyrosine kinases in the pathophysiology of cancer. Schlessinger J. (2000) Cell, 103:211-225; and Robinson et al. (2000) Oncogene, 19:5548-5557. MacKeigan and colleagues used a large-scale RNAi approach to identify kinases that might regulate survival and apoptosis of a human tumor cell line (HeLa), RNAi to ROR1 was found as one of the most potent in inducing apoptosis among the set of RNAi targeting each of 73 different kinase-encoding genes. MacKeigan et al. (2005) Nat Cell Biol., 7:591-600. However, these investigators did not examine the expression or function of ROR1 protein in these cells.

ROR1, receptor tyrosine kinase like orphan receptor one, is a molecule expressed at high levels during embryogenesis that plays a major role in the development of the skeleton, lungs and nervous system. ROR1 expression is greatly decreased in postpartum mammalian cells to levels that are barely detectable. ROR1 is a membrane-receptor with an intracellular kinase-like domain and extracellular Frizzled-like cysteine-rich domain, which is common to receptors of members of the Wnt-family. ROR1 is member of the ROR family that is evolutionarily conserved among *Caenorhavditis elegans, Drosophila*, mice and humans. Wilson C, Goberdhan D C, Steller H. Dror, a potential neurotrophic receptor gene, encodes a *Drosophila* homolog of the vertebrate Ror family of Trk-related receptor tyrosine kinases. Proc Natl Acad Sci USA. 1993; 90:7109-7113; Oishi et al. (1997) J Biol Chem., 272:11916-11923; Masiakowski et al. (1992) J Biol Chem., 267:26181-26190; Forrester et al. (2002) Cell Mol Life Sci., 59:83-96; and Oishi et al. (1999) Genes Cells, 4:41-56. The actual functional role of the ROR1 protein during embryogenesis is unknown, although it is believed to be a receptor for Wnt proteins that regulate cellular polarity and cell-to-cell interactions.

Although principally an embryonic protein, ROR1 is expressed uniquely on certain cancer cells, including in CLL, small lymphocytic lymphoma, marginal cell B-Cell lymphoma, Burkett's Lymphoma, and other cancers (e.g., breast cancers), but not on normal adult tissues and cells. In a recent study, it was found that ROR1, at both mRNA and protein level, was highly expressed in CLL B cells but not normal B cells. Moreover, it was found that ROR1 is a receptor for Wnt5a, which could induce activation of NF-κB when co-expressed with ROR1 in HEK293 cells and enhance survival of CLL cells in vitro. This indicates that ROR1 is a CLL survival-signaling receptor for Wnt5a. Another study found that ROR1 was expressed in acute lymphocytic leukemia (ALL) as well. Shabani et al. (2007) Tumour Biol., 28:318-326; and Baskar et al. (2008) Clin Cancer Res., 14:396-404. Expression of ROR1 protein has now been demonstrated on a variety of hematologic and solid tumor cancers.

Therapeutic control of ROR1 expression is necessary. However, although polyclonal anti-ROR1 antibodies raised against ROR1 peptide are commercially available. The inventors developed a monoclonal anti-ROR1 antibody, terms 4A5, which reacts with the native ROR1 protein and is capable of detecting cell-surface expression of ROR1 for flow cytometric analysis. However, robustly therapeutic antibodies with demonstrable ability to inhibit ROR-1 mediated cancer cell proliferation to a degree that is therapeutically significant for slowing or preventing growth and metastasis have not been available.

SUMMARY OF THE INVENTION

The invention provides antibodies and combination of antibodies for in vivo and in vitro inhibition of ROR-1 cell mediated proliferation of cells from subjects with cancer, including lymphomas, CLL, small lymphocytic lymphoma, marginal cell B-Cell lymphoma, Burkett's Lymphoma, renal cell carcinoma, colon cancer, colorectal cancer, breast cancer, epithelial squamous cell cancer, melanoma, myeloma, stomach cancer, brain cancer, lung cancer, pancreatic cancer, cervical cancer, ovarian cancer, liver cancer, bladder cancer, prostate cancer, testicular cancer, thyroid cancer, and head and neck cancer, but not in blood or splenic lymphocytes of nonleukemic patients or normal adults.

The antibodies of the invention are also useful for differentiation between ROR1 expressing cancer cells ("ROR1 cancer") and normal cells. For example, an immunoassay that detects ROR1 in a sample from a subject by contacting the sample with a ROR1-specific antibody of the invention and detecting immunoreactivity between the antibody and ROR1 in the sample is provided.

In accordance with a further aspect of the invention, a ROR1 cancer is diagnosed in a subject by detecting the presence or quantity of ROR1 protein in a sample.

The present invention includes compositions that include purified, isolated monoclonal antibodies and combinations thereof that bind specifically to ROR1 receptor protein.

Bottom panel depicts the relative ROR1 expression (x axis) using the mouse anti-ROR1 4A5 mAb.

Figure 1:
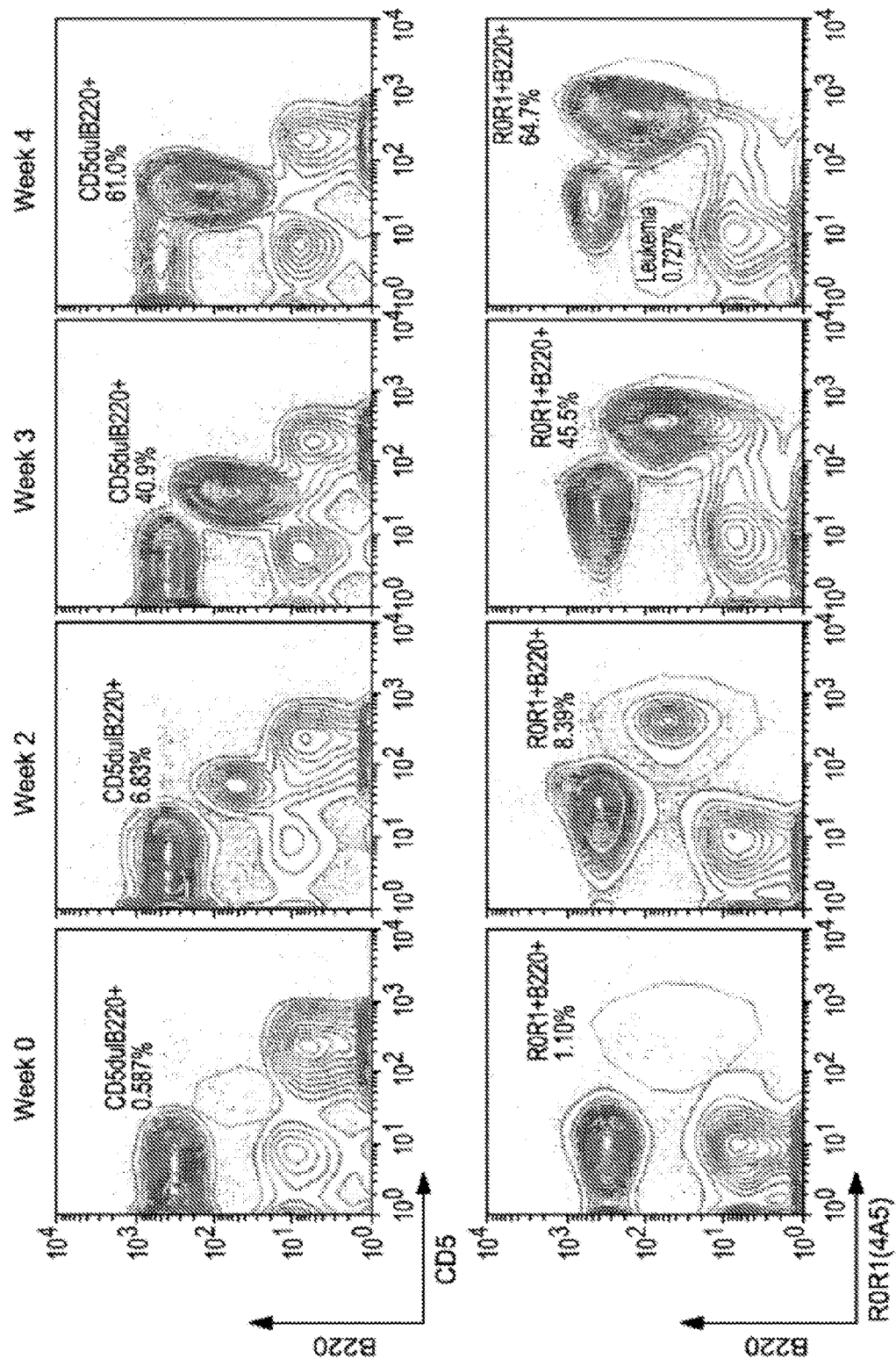
FIG. 1 is a series of graphs illustrating the results of flow cytometric analysis of the expansion of CD5+B220low leukemia B cells in ROR1 Tg mice following the adoptive transfer of $1\times10^7$ splenocytes from a ROR1×TCL1 Tg mouse. Upper panel depicts the expansion from 2 to 4 weeks following adoptive transfer. Percentage of leukemic cells on the contour plot of mCD5 (x-axis) vs mB220 (y-axis) is indicated on above the gate on CD5$^+$B220$^{low}$ lymphocytes.
Figure 2:
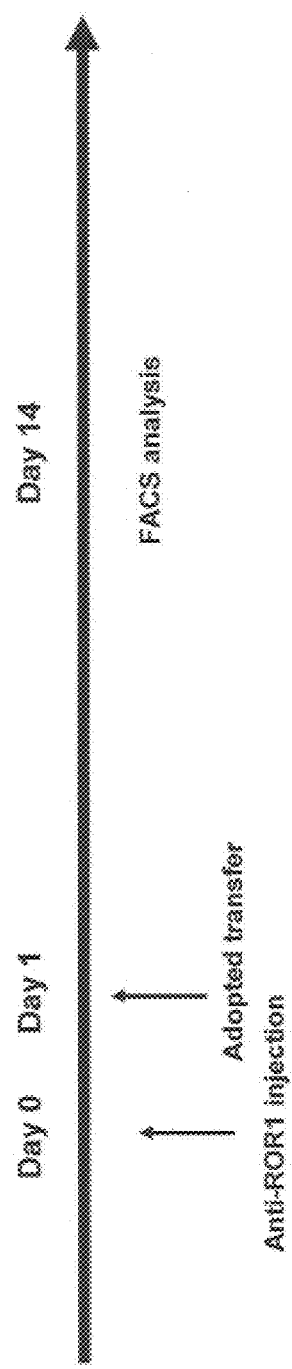

FIG. 2 is a diagram outlining the analysis of anti-ROR1 mAb on the adoptive transfer and engragment of ROR1× TCL1 leukemic splenocytes. ROR1 Tg mice (4 mice/group) were given 250 ug of 4A5, D10 or control mIgG i.v. on day 0. The following day, 1×10$^7$ splenocytes from a ROR1× TCL1 Tg mouse were adoptively transferred i.v. All mice were subsequently monitor weekly for expansion of CD5$^+$ B220$^{low}$ leukemic B cells by flow cytometry beginning at 2 weeks post transfer.

Figure 3:
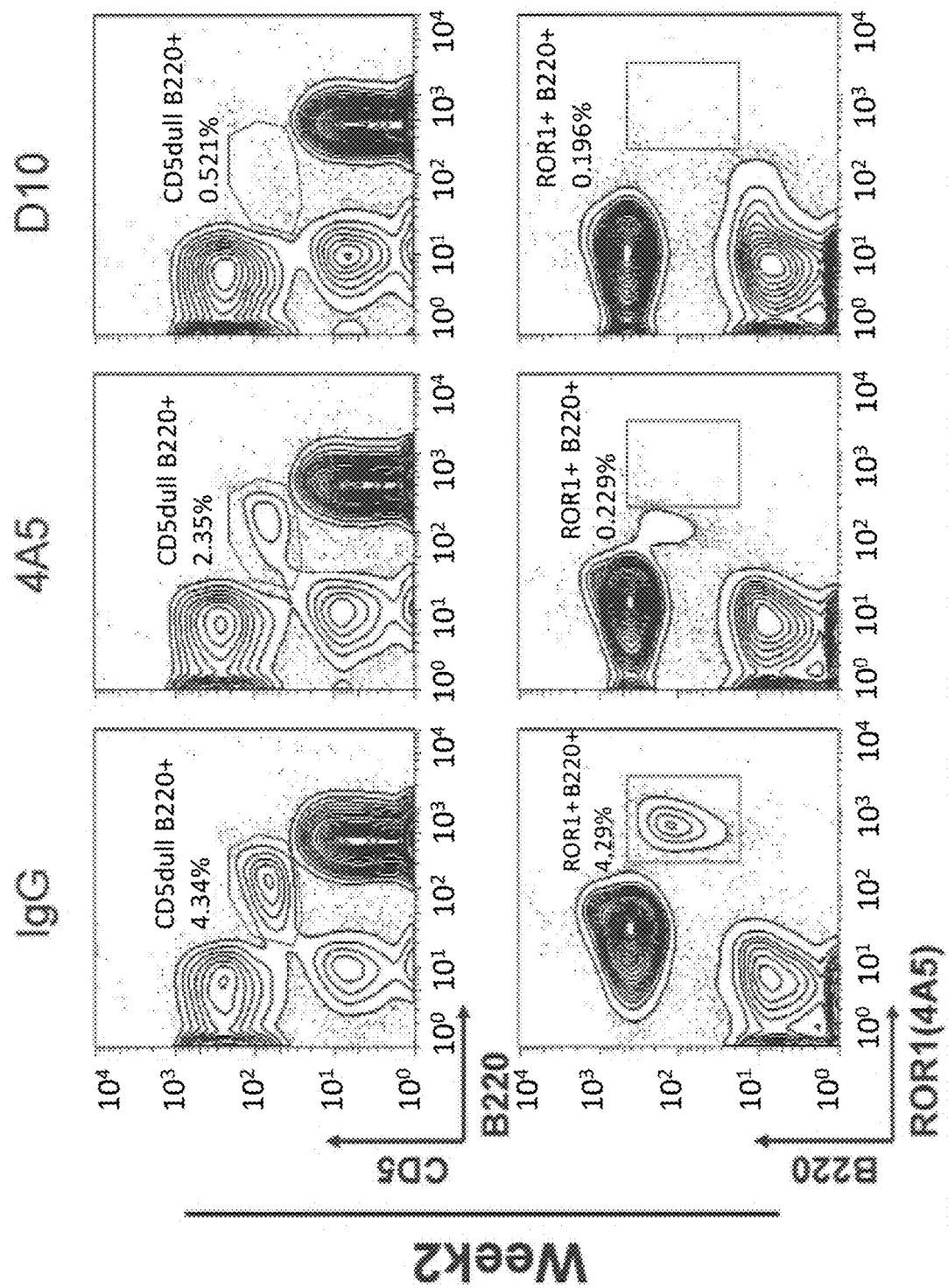

FIG. 3 is a series of graphs illustrating the results of a flow cytometric analysis which demonstrate that anti-ROR1 antibodies of the invention inhibited the development of CLL-like leukemia in ROR1 Tg mice. 2 weeks after adoptive transfer, the PBMC facs analysis were performed. The data showed the anti-ROR1 antibody D10 but not anti-ROR1 antibody 4A5 could markedly inhibit the CD5$^{dull}$B220$^+$ and ROR1$^{bright}$B220$^+$ leukemic B cell expansion.

Figure 4:
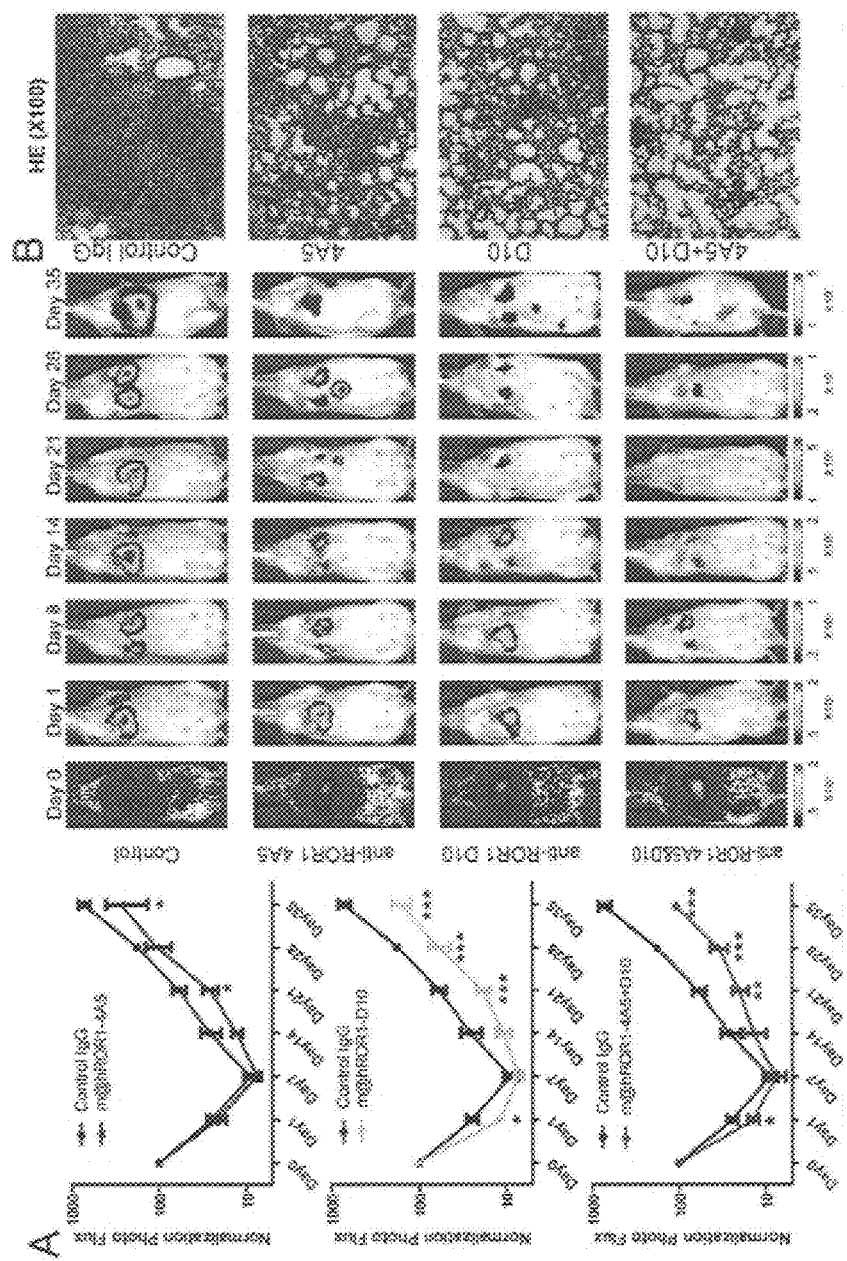

FIG. 4 panels A and B show a series of graphs illustrating the results of in vivo testing in a murine model of human breast cancer. The anti-ROR1 antibodies inhibited breast cancer metastasis in rag–/– g–/– deficiency mice. 5E5 MDA-MB-231 breast cancer cell were transferred by i.v. injection to rag–/– g–/– mice on day 1. The rag–/– g–/– deficiency mice were also i.v. injected isotype control or anti-ROR1 antibody (4A5, D10, and 4A5 plus D10) on day 1, 3, 7 and 14 at 100 mg per mice. FIG. 4 (center panel) also provides images from IVIS in vivo imaging procedures on the above mice, which were performed every week. 5 weeks later, the mice were sacrificed and histology analysis were performed (FIG. 4 panel B). The anti-ROR1 antibody D10 and the antibody combination (4A5 plus D10) both significantly inhibited metastasis of the breast cancer, with inhibition by D10 alone being greater than inhibition by 4a5 alone.

Figure 5:
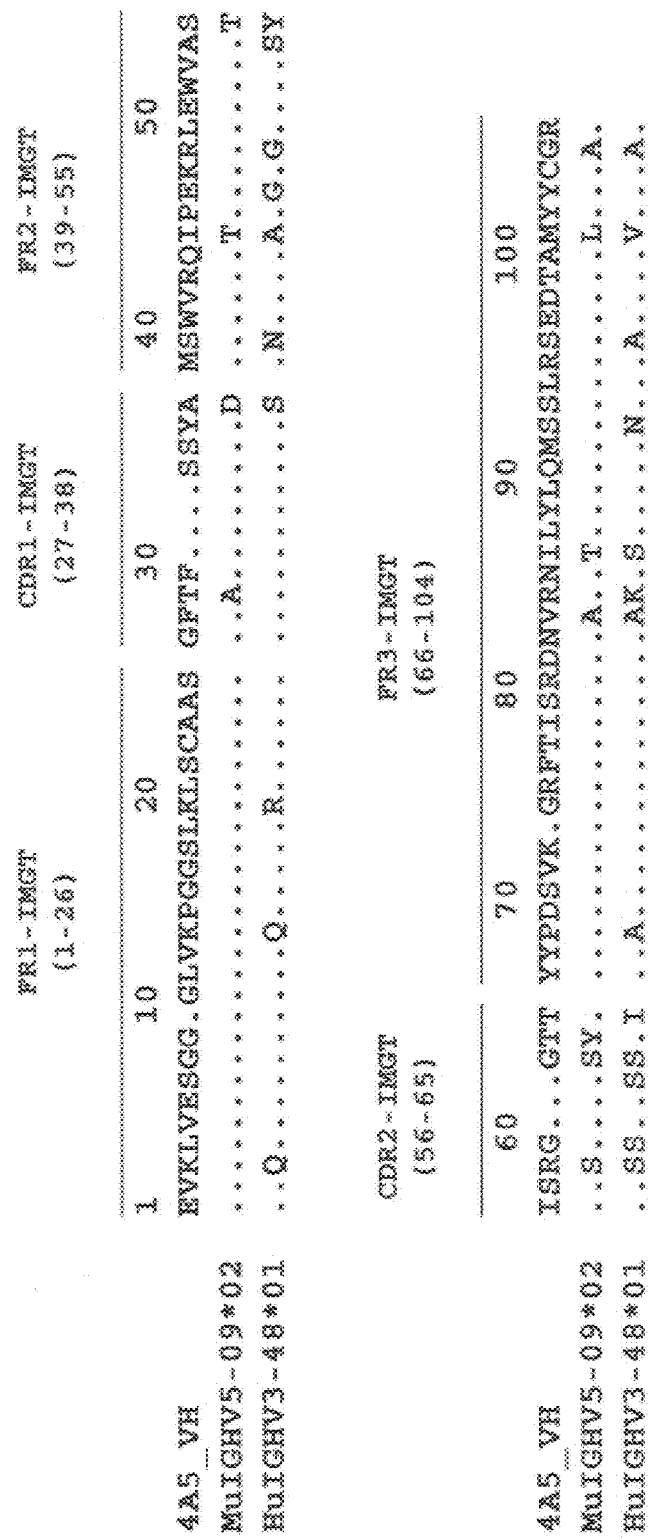

FIG. 5 provides a nucleotide coding sequence comparison of 4A5 Ig heavy chain (VH) to the closest germline mouse and human immunoglobulin (Ig) VH.

Figure 6:
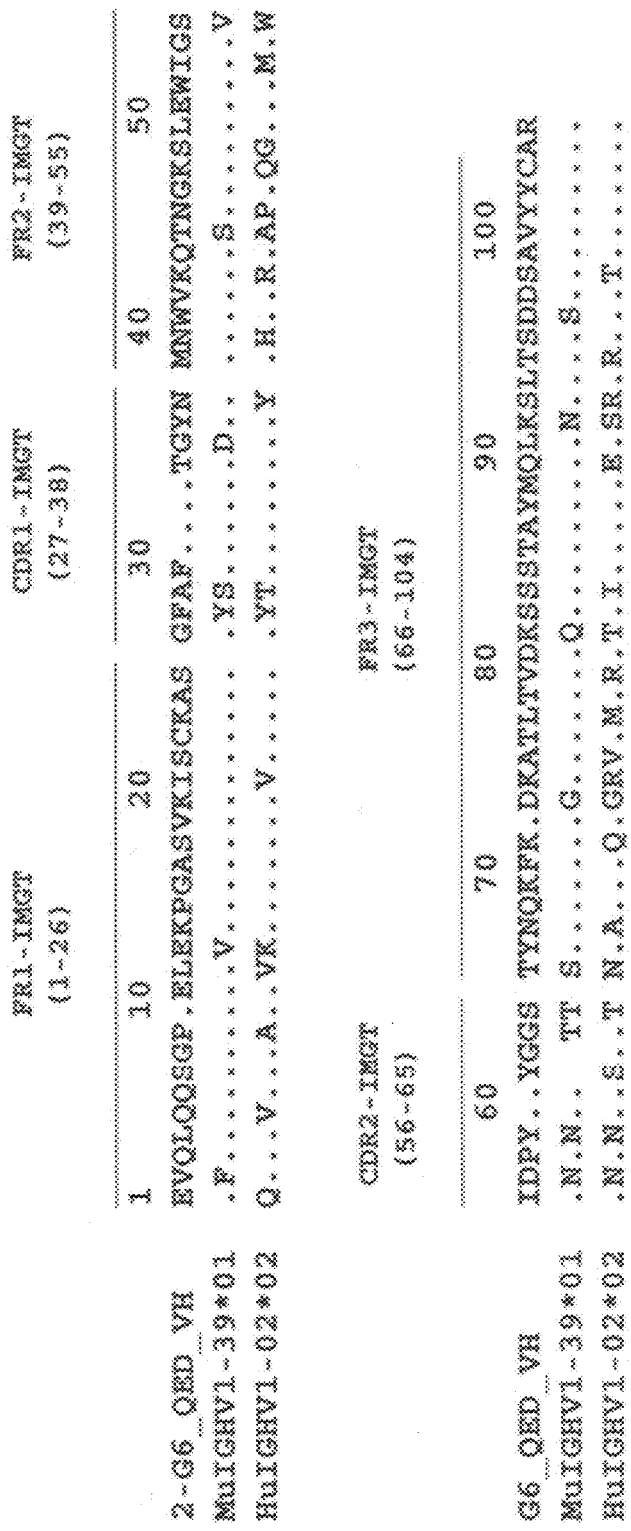

FIG. 6 provides a nucleotide coding sequence comparison of G6 Ig heavy chain (VH) to the closest germline mouse and human immunoglobulin (Ig) VH.

Figure 7:
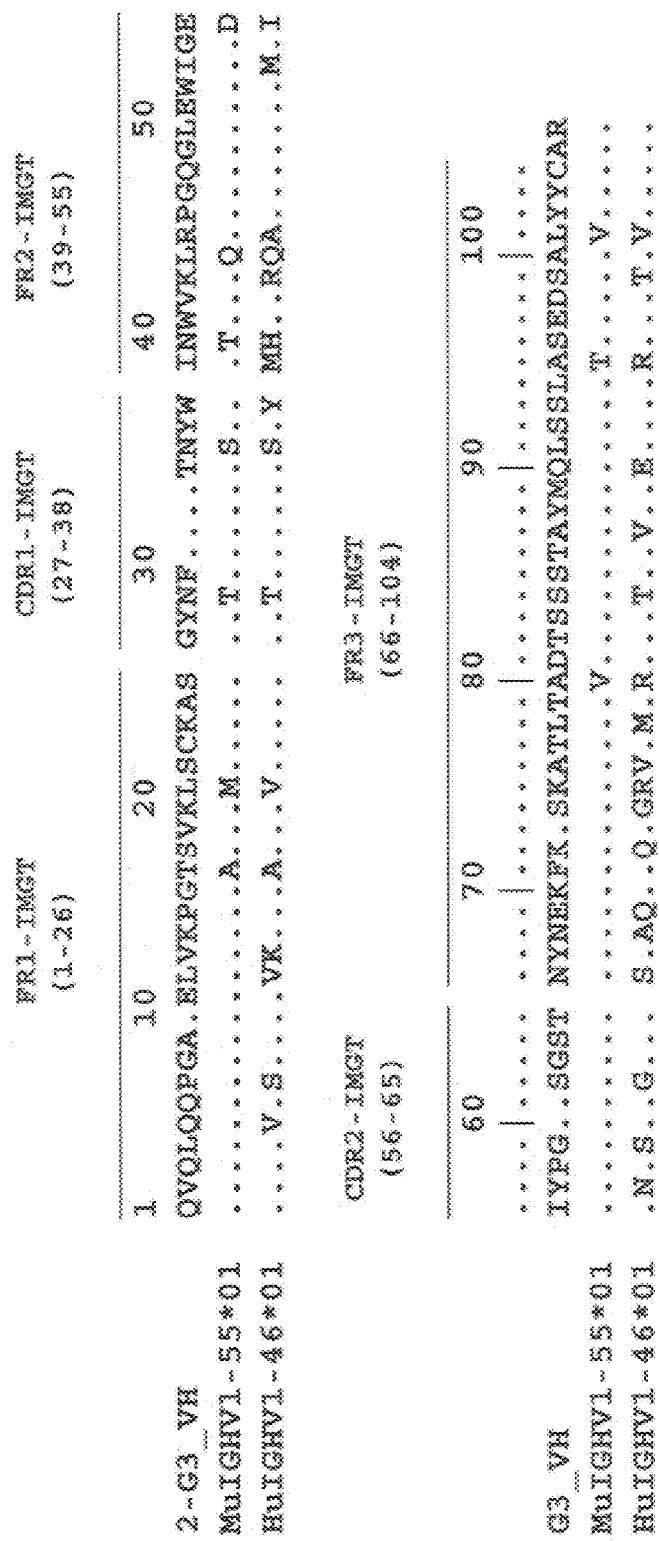

FIG. 7 provides a nucleotide coding sequence comparison of G3 Ig heavy chain (VH) to the closest germline mouse and human immunoglobulin (Ig) VH.

Figure 8:
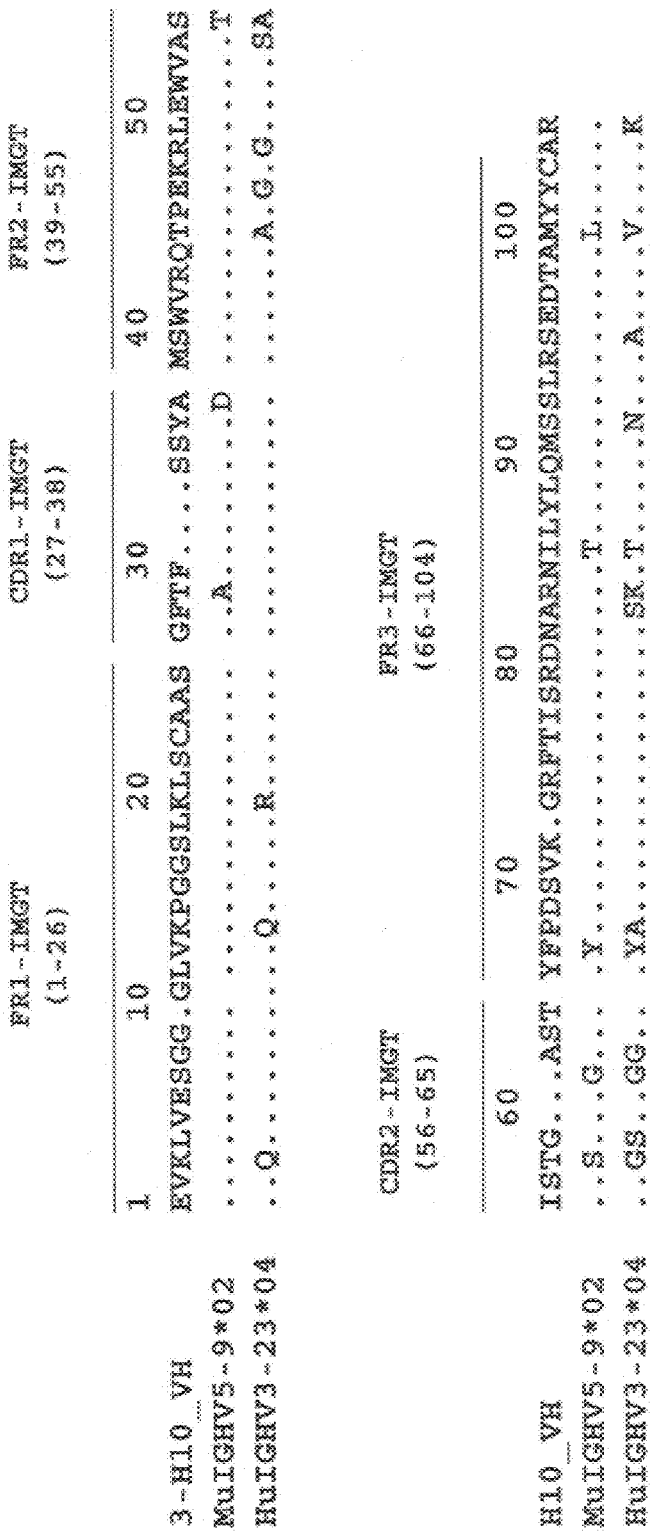

FIG. 8 provides a nucleotide coding sequence comparison of H10 Ig heavy chain (VH) to the closest germline mouse and human immunoglobulin (Ig) VH.

Figure 9:
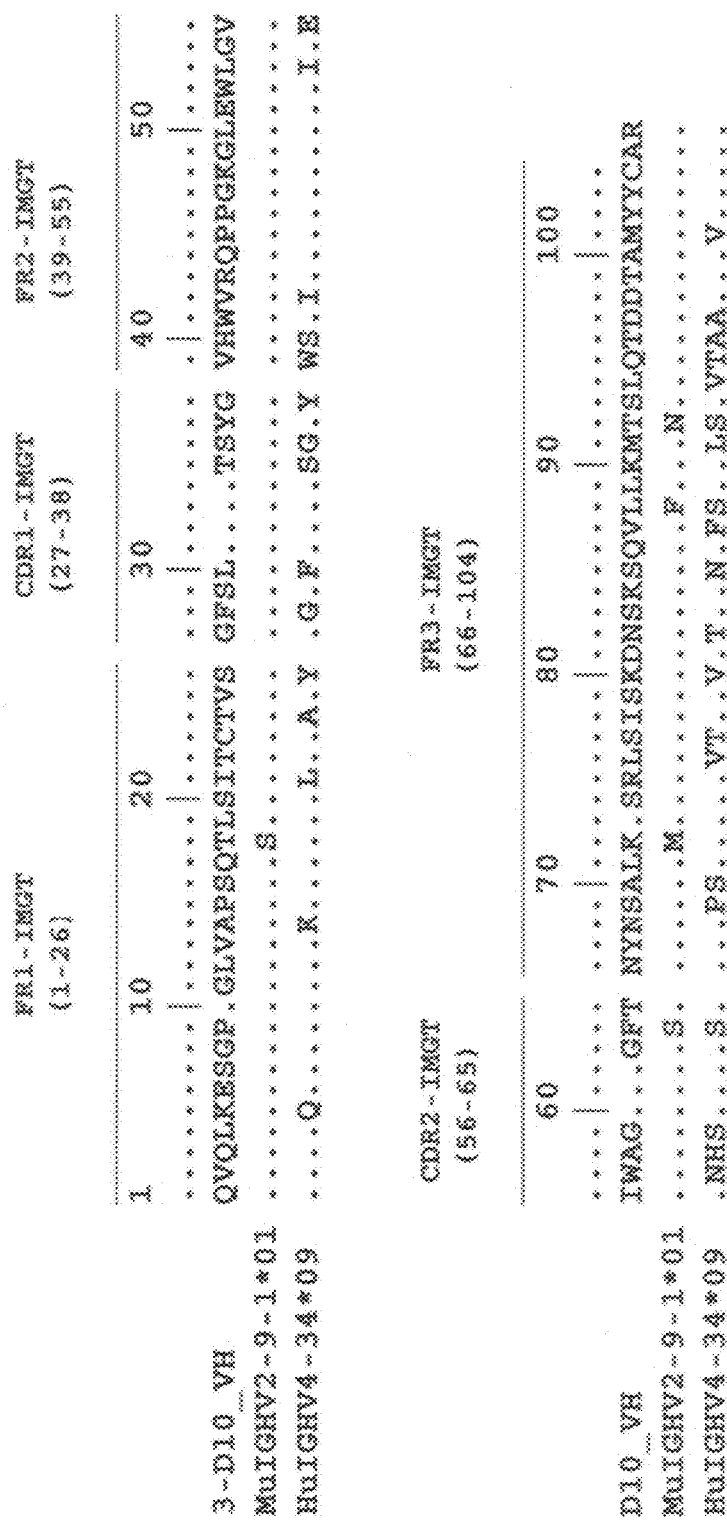

FIG. 9 provides a nucleotide coding sequence comparison of D10 Ig heavy chain (VH) to the closest germline mouse and human immunoglobulin (Ig) VH.

Figure 10:
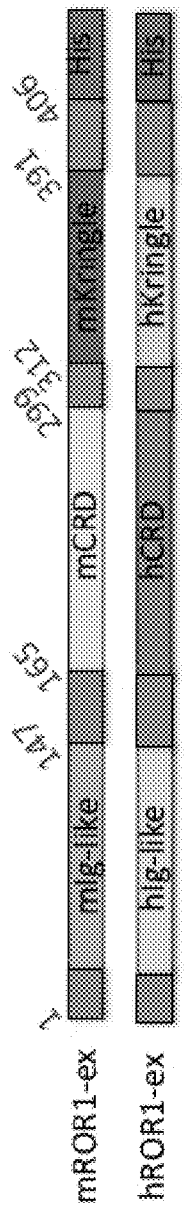

FIG. 10 is a diagram and chart depicting the highly conserved nature of human and murine ROR1.

FIG. 11 is a nucleotide comparison depicting the domain structure and sequence homology of human and murine ROR1 extracellular protein.

FIG. 12 is a chart indicating the extracellular domain which the anti-ROR1 mAbs bind the ROR1 protein.

Figure 13:
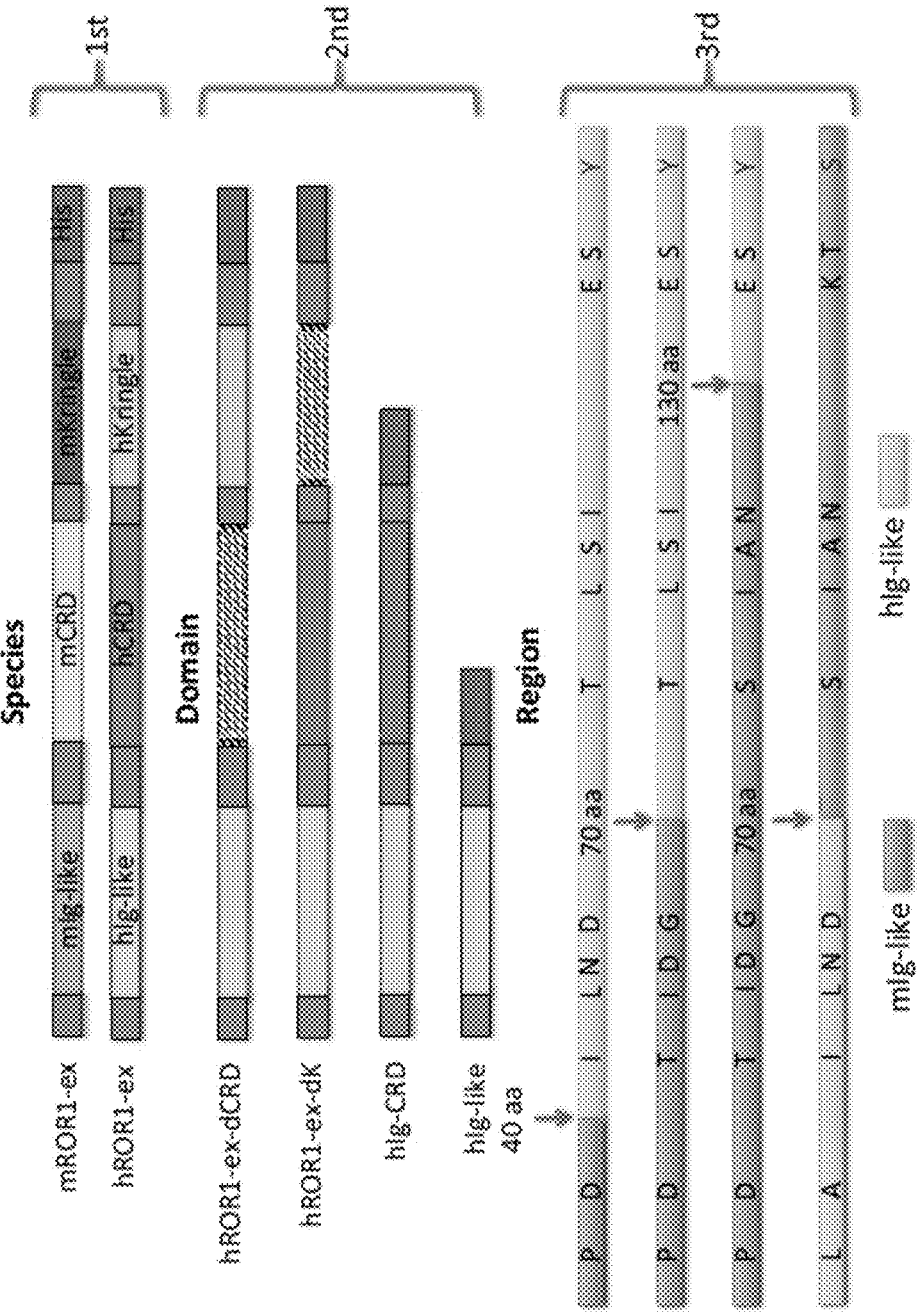

FIG. 13 is a diagram depicting the chimeric ROR1 proteins generated to determine the binding domain of each of the anti-ROR1 mAbs.

Figure 14:
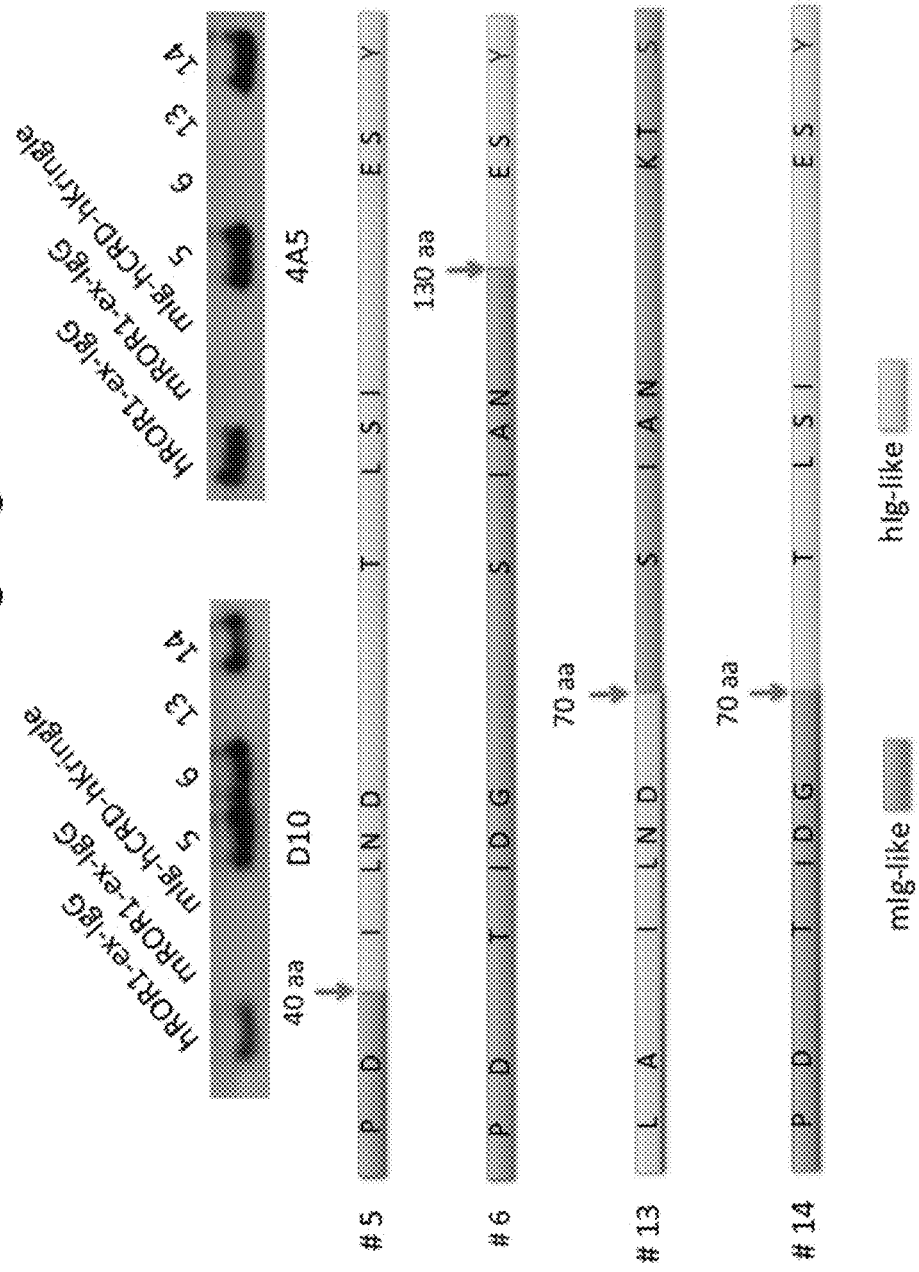

FIG. 14 is a diagram depicting the truncated ROR1 proteins generated to determine the sub-regions which each of the anti-ROR1 mAbs binds.

Figure 15:
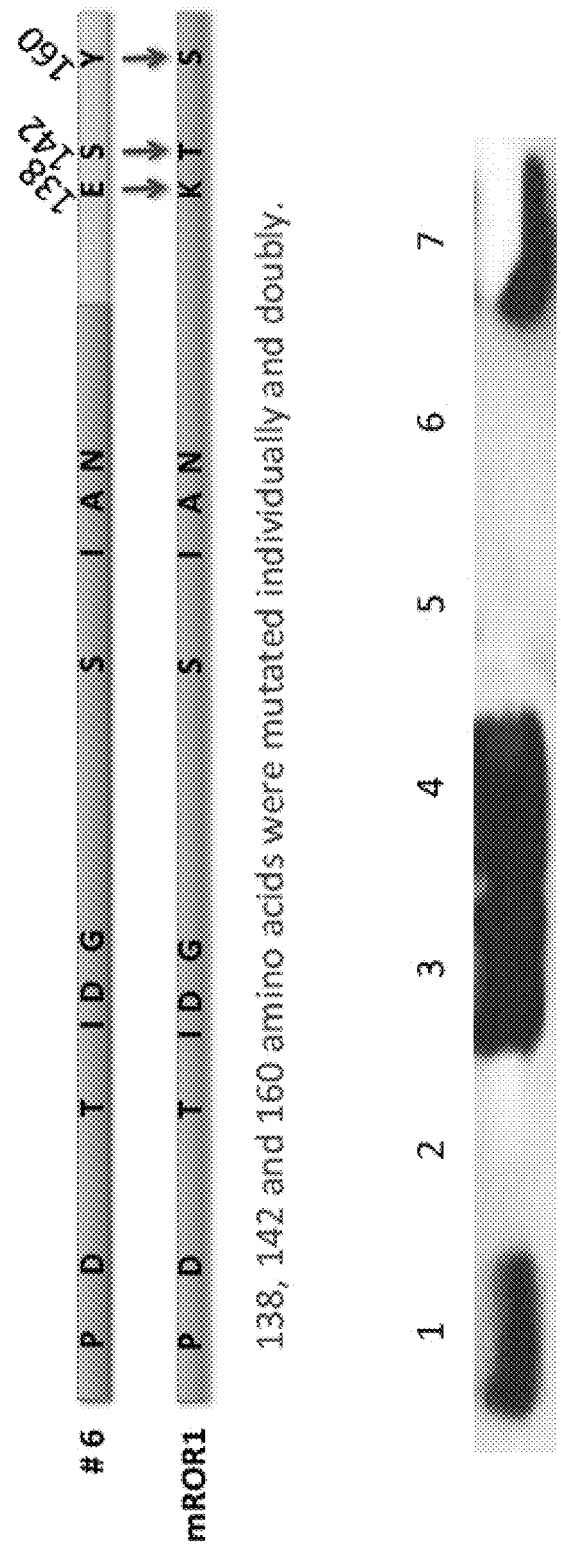

FIG. 15 is a diagram depicting the amino acids which were murinized to determine residues critical for mAb binding to human ROR1 and a western blot showing that the 138 glutamic acid residue is critical for antibody D10 binding to human ROR1.

FIGS. 16A-16B are graphs indicating the K$_D$ values for antibody D10 (FIG. 16A) and 4A5 (FIG. 16B).

FIG. 17 is a series of graphs illustrating the anti-ROR1 antibody D10 is highly active in in vivo assays.

Figure 18:
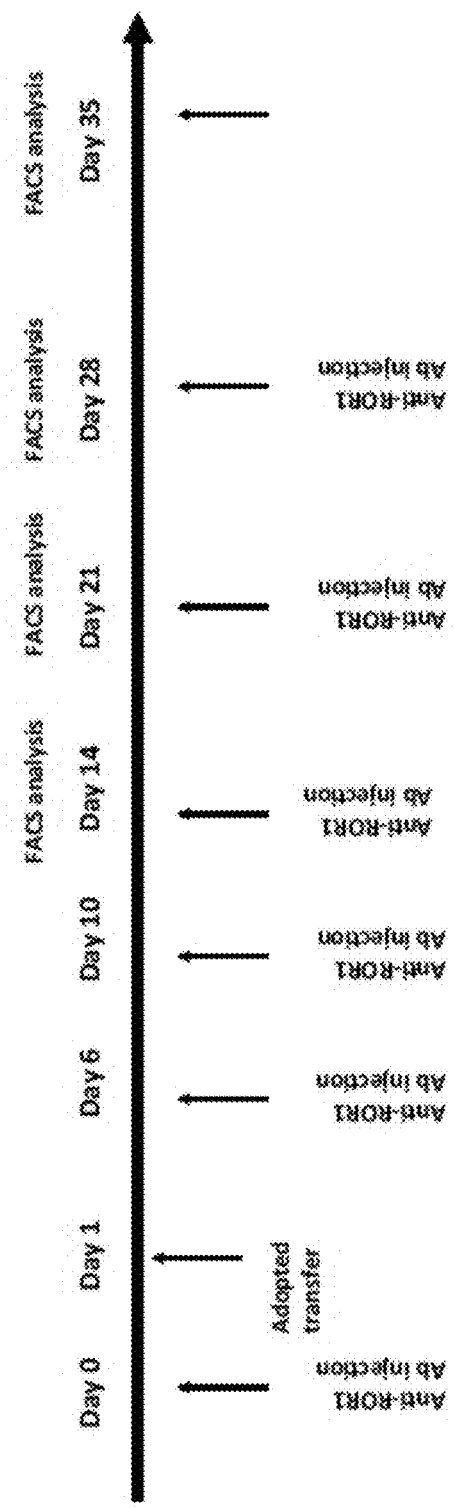

FIG. 18 is a diagram outlining the analysis of anti-ROR1 mAb on the adoptive transfer and engragment of ROR1× TCL1 leukemic splenocytes. ROR1 Tg mice (5 mice/group) were given 250 ug of 4A5, D10 or control mIgG i.v. on day 0. The following day, 5×10$^5$ splenocytes from a ROR1× TCL1 Tg mouse were adoptively transferred i.v. All mice were subsequently monitored weekly for expansion of CD5$^{dull}$B200$^+$ leukemic B cells by flow cytometery beginning at 2 weeks post transfer.

Figure 19:
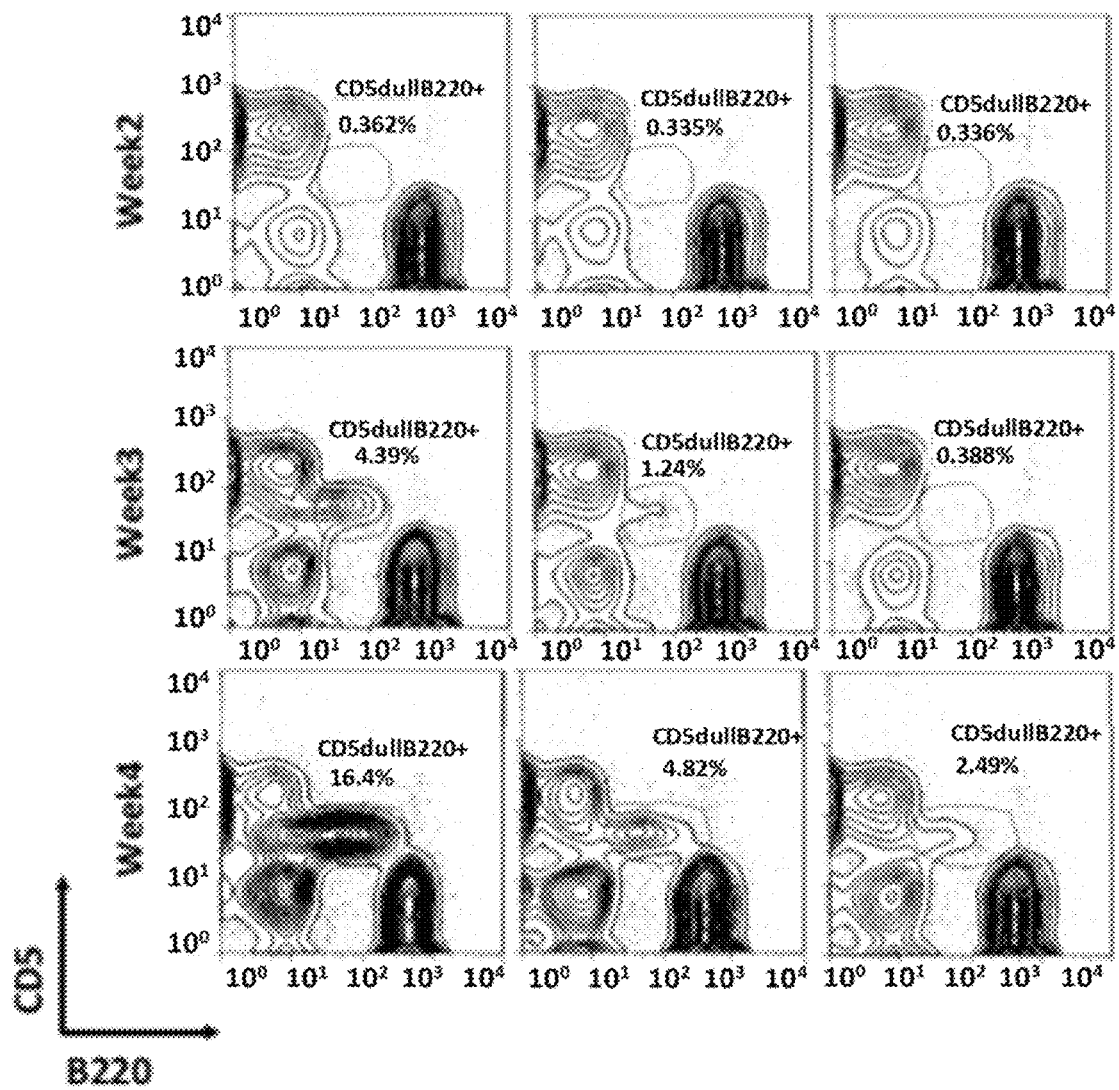

FIG. 19 a series of graphs illustrating the results of flow cytometric analysis of the anti-ROR1 antibodies inhibiting the development of CLL-like leukemia in ROR1 Tg mice. 2 weeks after adoptive transfer, the PBMC facs analysis were performed. The data showed the anti-ROR1 antibody D10 but not anti-ROR1 antibody 4A5 could markedly inhibit the CD5$^{dull}$B220$^+$ and ROR1$^{bright}$B220$^+$ leukemic B cell expansion.

Figure 20:
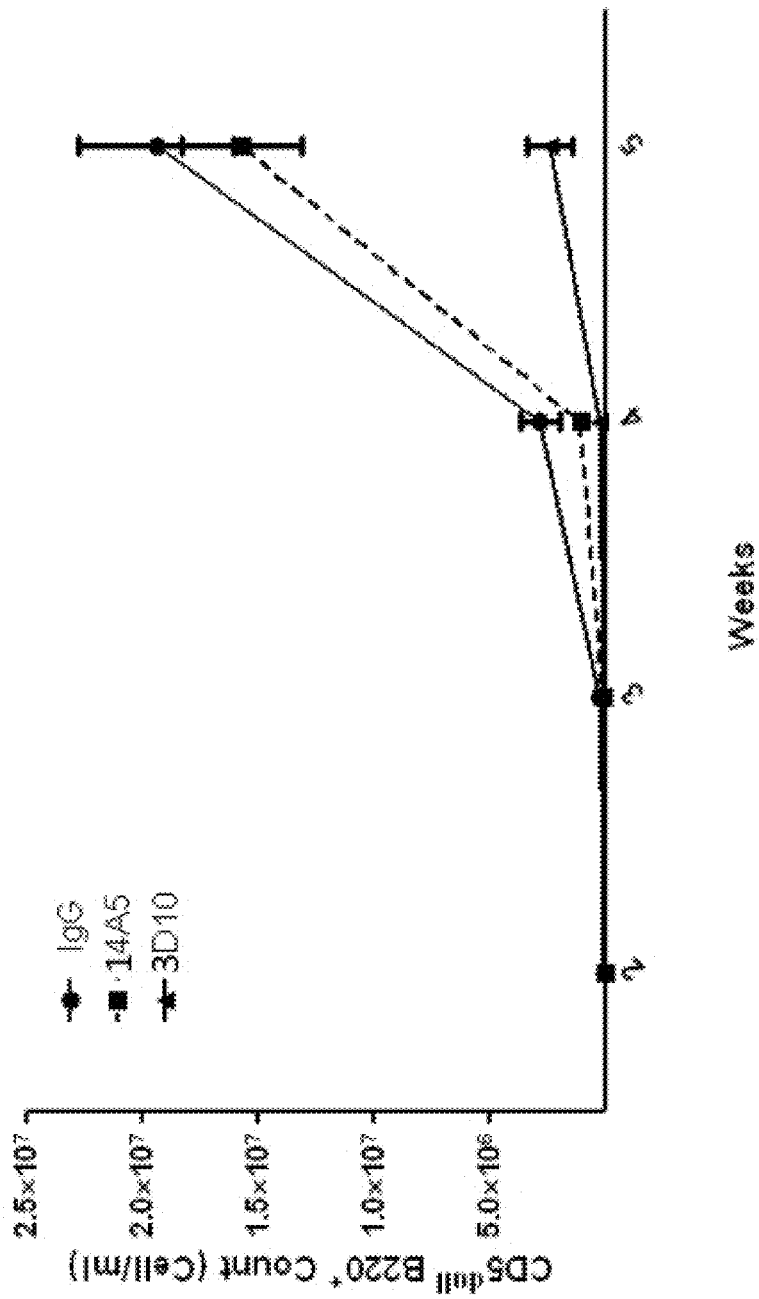

FIG. 20 is a graph illustrating that anti-ROR1 antibody D10 inhibits the development and expansion of ROR1× TCL1 leukemic B cells in the blood of recipient animals until two weeks after receiving the last infusion of the mAb.

Figure 21:
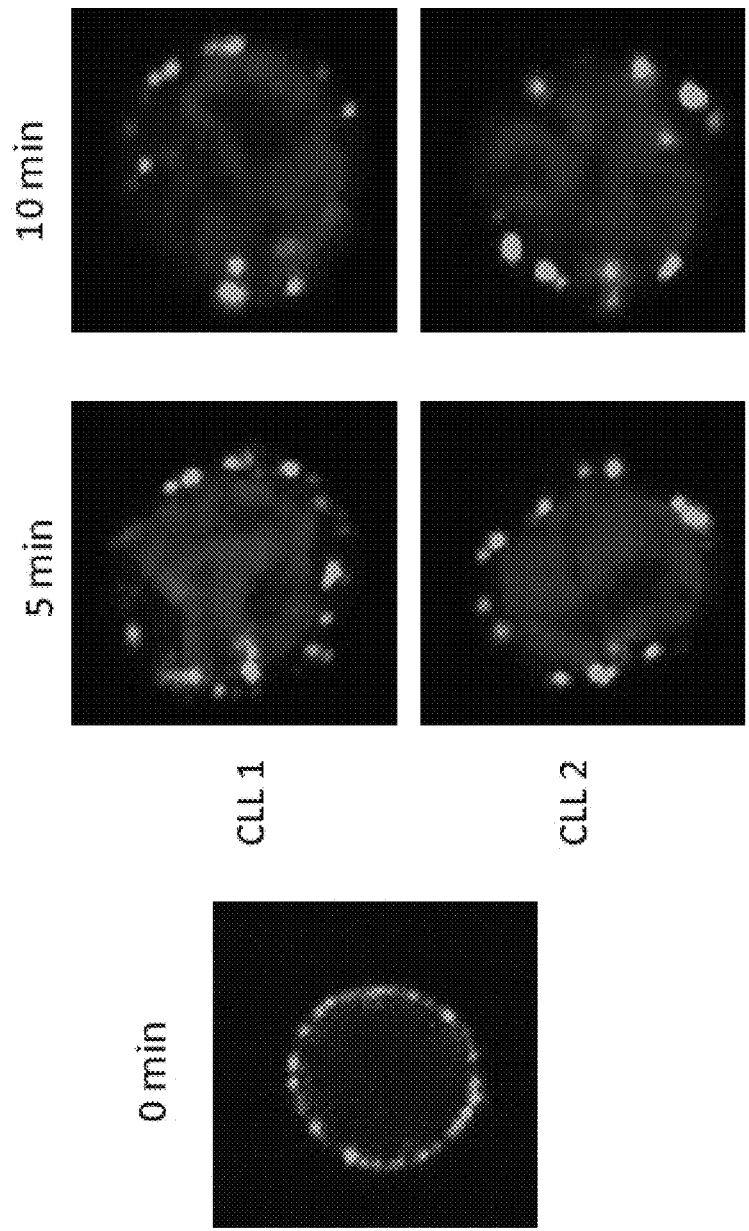

FIG. 21 is a depiction of the rapid internalization of the anti-ROR1 antibody D10 into CLL cells.

Figure 22:
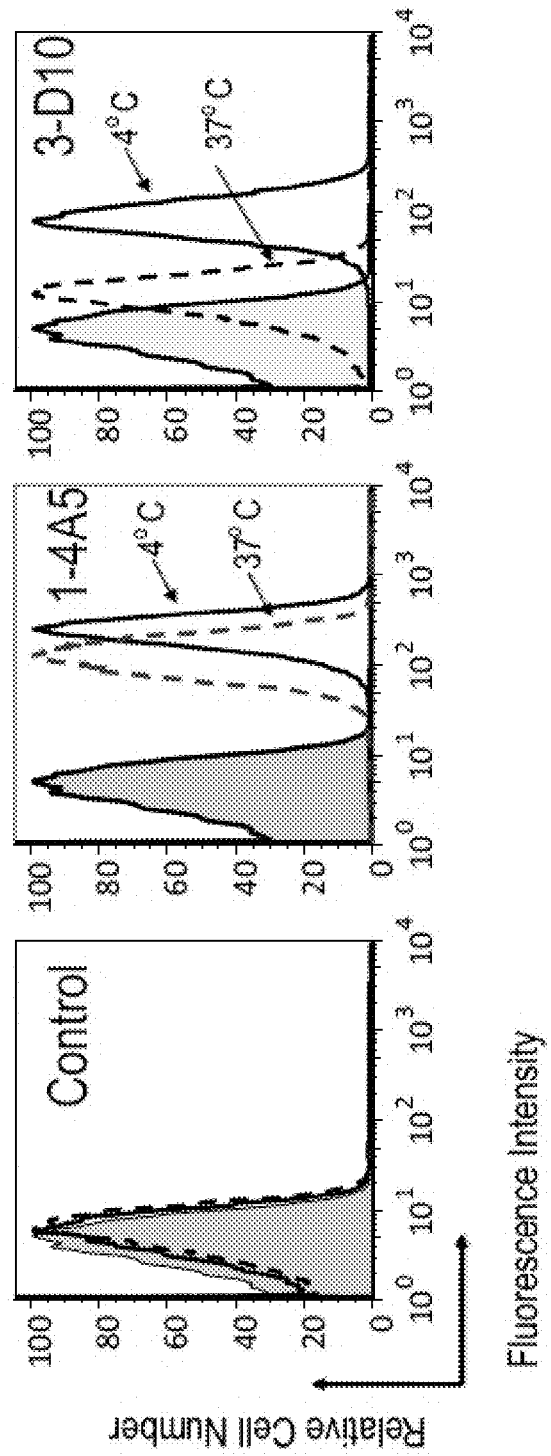

FIG. 22 is a series of graphs illustrating the results of flow cytometric analysis showing that anti-ROR1 antibodies D10 and 4A5 are both internalized into CLL cells. CLL cells were incubated with mouse anti-hROR1 Ab-Alex647 for 30 min at 4° C. Subsequently the cells were washed and either left at 4° C. or incubated for 4 hours at 37° C., followed by flow cytometry. The background signal with non-staining is also shown.

Figure 23:
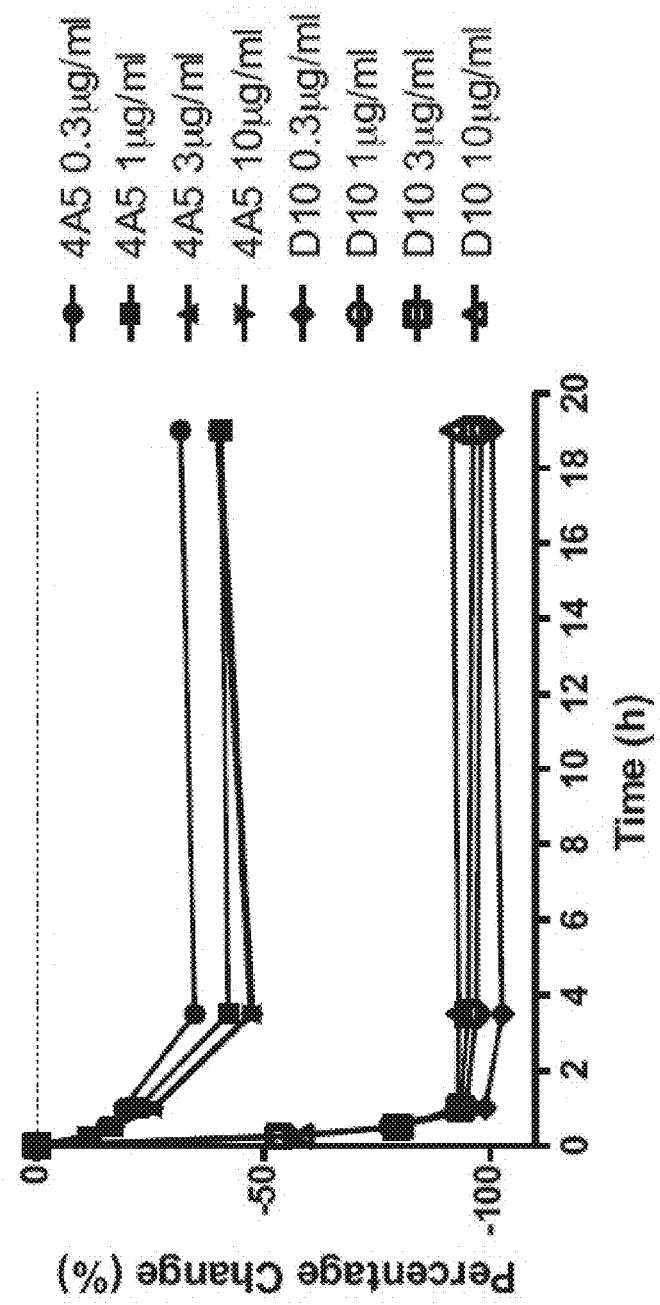

FIG. 23 is a graph illustrating the kinetics of the internalization of anti-ROR1 antibodies D10 and 4A5.

Figure 24:
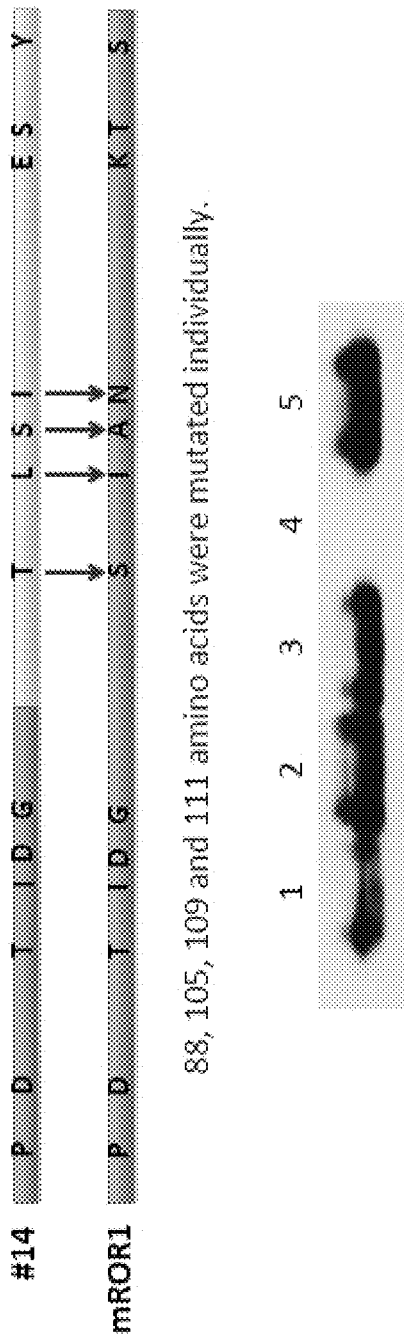

FIG. 24 is a diagram depicting the amino acids which were murinized to determine residues critical for mAb binding to human ROR1 and a western blot showing that the 111 isoleucine residue is critical for antibody 4A5 binding to human ROR1.

DETAILED DESCRIPTION OF THE PREFERRED EMBODIMENTS

The presently disclosed subject matter are described more fully below. However, the presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated FIGS. Therefore, it is to be understood that the presently disclosed subject matter is not to be limited to the specific embodiments disclosed and that modifications and other embodiments are intended to be included within the scope of the appended claims.

Antibodies of the invention were produced monoclonally using techniques as previously described. Briefly, Naturally occurring antibodies are generally tetramers containing two light chains and two heavy chains. Experimentally, antibodies can be cleaved with the proteolytic enzyme papain, which causes each of the heavy chains to break, producing three separate subunits. The two units that consist of a light chain and a fragment of the heavy chain approximately equal in mass to the light chain are called the Fab fragments (i.e., the antigen binding fragments). The third unit, consisting of two equal segments of the heavy chain, is called the Fc fragment. The Fc fragment is typically not involved in antigen-antibody binding, but is important in later processes involved in ridding the body of the antigen.

Because Fab and F(ab')$_2$ fragments are smaller than intact antibody molecules, more antigen-binding domains are available than when whole antibody molecules are used. Proteolytic cleavage of a typical IgG molecule with papain is known to produce two separate antigen binding fragments called Fab fragments which contain an intact light chain linked to an amino terminal portion of the contiguous heavy chain via by disulfide linkage. The remaining portion of the papain-digested immunoglobin molecule is known as the Fc fragment and consists of the carboxy terminal portions of the antibody left intact and linked together via disulfide bonds. If an antibody is digested with pepsin, a fragment known as an F(ab')$_2$ fragment is produced which lacks the Fc region but contains both antigen-binding domains held together by disulfide bonds between contiguous light and heavy chains (as Fab fragments) and also disulfide linkages between the remaining portions of the contiguous heavy chains (Handbook of Experimental Immunology. Vol 1: Immunochemistry, Weir, D. M., Editor, Blackwell Scientific Publications, Oxford (1986)).

As readily recognized by those of skill in the art, altered antibodies (e.g., chimeric, humanized, CDR-grafted, bifunctional, antibody polypeptide dimers (i.e., an association of two polypeptide chain components of an antibody, e.g., one arm of an antibody including a heavy chain and a light chain, or an Fab fragment including VL, VH, CL and CH antibody domains, or an Fv fragment comprising a VL domain and a VH domain), single chain antibodies (e.g., an scFv (i.e., single chain Fv) fragment including a VL domain linked to a VH domain by a linker, and the like) can also be produced by methods well known in the art.

Monoclonal antibody (mAb) technology can be used to obtain mAbs to ROR1. Briefly, hybridomas are produced using spleen cells from mice immunized with ROR1 antigens. The spleen cells of each immunized mouse are fused with mouse myeloma Sp 2/0 cells, for example using the polyethylene glycol fusion method of Galfre, G. and Milstein, C., Methods Enzymol., 73:3-46 (1981). Growth of hybridomas, selection in HAT medium, cloning and screening of clones against antigens are carried out using standard methodology (Galfre, G. and Milstein, C., Methods Enzymol., 73:3-46 (1981)).

HAT-selected clones are injected into mice to produce large quantities of mAb in ascites as described by Galfre, G. and Milstein, C., Methods Enzymol., 73:3-46 (1981), which can be purified using protein A column chromatography (BioRad, Hercules, Calif.). mAbs are selected on the basis of their (a) specificity for ROR1, (b) high binding affinity, (c) isotype, and (d) stability.

mAbs can be screened or tested for ROR1 specificity using any of a variety of standard techniques, including Western Blotting (Koren, E. et al., Biochim. Biophys. Acta 876:91-100 (1986)) and enzyme-linked immunosorbent assay (ELISA) (Koren, E. et al., Biochim. Biophys. Acta 876:91-100 (1986)).

Humanized forms of mouse antibodies can be generated by linking the CDR regions of non-human antibodies to human constant regions by recombinant DNA techniques (see, e.g., Queen et al., Proc. Natl. Acad. Sci. USA 86:10029-10033, 1989 and WO 90/07861, each incorporated by reference). Human antibodies can be obtained using phage-display methods (see, e.g., Dower et al., WO 91/17271; McCafferty et al., WO 92/01047). In these methods, libraries of phage are produced in which members display different antibodies on their outer surfaces. Antibodies are usually displayed as Fv or Fab fragments. Phage displaying antibodies with a desired specificity may be selected by affinity enrichment.

Human antibodies may be selected by competitive binding experiments, or otherwise, to have the same epitope specificity as a particular mouse antibody. Using these techniques, a humanized ROR1 antibody having the human IgG1 constant region domain and the human kappa light chain constant region domain with the mouse heavy and light chain variable regions. The humanized antibody has the binding specificity of a mouse ROR1 mAb, specifically the 4A5 mAb described in Examples 4 and 5.

It may be desirable to produce and use functional fragments of a mAb for a particular application. The well-known basic structure of a typical IgG molecule is a symmetrical tetrameric Y-shaped molecule of approximately 150,000 to 200,000 daltons consisting of two identical light polypeptide chains (containing about 220 amino acids) and two identical heavy polypeptide chains (containing about 440 amino acids). Heavy chains are linked to one another through at least one disulfide bond. Each light chain is linked to a contiguous heavy chain by a disulfide linkage. An antigen-binding site or domain is located in each arm of the Y-shaped antibody molecule and is formed between the amino terminal regions of each pair of disulfide linked light and heavy chains. These amino terminal regions of the light and heavy chains consist of approximately their first 110 amino terminal amino acids and are known as the variable regions of the light and heavy chains. In addition, within the variable regions of the light and heavy chains there are hypervariable regions which contain stretches of amino acid sequences, known as complementarity determining regions (CDRs). CDRs are responsible for the antibody's specificity for one particular site on an antigen molecule called an epitope. Thus, the typical IgG molecule is divalent in that it can bind two antigen molecules because each antigen-binding site is able to bind the specific epitope of each antigen molecule. The carboxy terminal regions of light and heavy chains are similar or identical to those of other antibody molecules and are called constant regions. The amino acid sequence of the constant region of the heavy chains of a particular antibody defines what class of antibody it is, for example, IgG, IgD, IgE, IgA or IgM. Some classes of antibodies contain two or more identical antibodies associated with each other in multivalent antigen-binding arrangements.

Fab and F(ab')$_2$ fragments of mAbs that bind ROR1 can be used in place of whole mAbs. Because Fab and F(ab')$_2$ fragments are smaller than intact antibody molecules, more antigen-binding domains are available than when whole antibody molecules are used. Proteolytic cleavage of a typical IgG molecule with papain is known to produce two separate antigen binding fragments called Fab fragments which contain an intact light chain linked to an amino terminal portion of the contiguous heavy chain via by disulfide linkage. The remaining portion of the papain-digested immunoglobin molecule is known as the Fc fragment and consists of the carboxy terminal portions of the antibody left intact and linked together via disulfide bonds. If an antibody is digested with pepsin, a fragment known as an F(ab')₂ fragment is produced which lacks the Fc region but contains both antigen-binding domains held together by disulfide bonds between contiguous light and heavy chains (as Fab fragments) and also disulfide linkages between the remaining portions of the contiguous heavy chains (Handbook of Experimental Immunology. Vol 1: Immunochemistry, Weir, D. M., Editor, Blackwell Scientific Publications, Oxford (1986)).

With respect to particular antibodies, "specific binding" refers to antibody binding to a predetermined antigen. Typically, the antibody binds with an affinity corresponding to a $K_D$ of about $10^{-8}$ M or less, and binds to the predetermined antigen with an affinity (as expressed by $K_D$) that is at least 10 fold less, and preferably at least 100 fold less than its affinity for binding to a non-specific antigen (e.g., BSA, casein) other than the predetermined antigen or a closely-related antigen. Alternatively, the antibody can bind with an affinity corresponding to a $K_A$ of about $10^6$ M$^{-1}$, or about $10^7$ M$^{-1}$, or about $10^8$ M$^{-1}$, or $10^9$ M$^{-1}$ or higher, and binds to the predetermined antigen with an affinity (as expressed by $K_A$) that is at least 10 fold higher, and preferably at least 100 fold higher than its affinity for binding to a non-specific antigen (e.g., BSA, casein) other than the predetermined antigen or a closely-related antigen.

Also, reference to "an antibody having binding specificity for ROR-1 protein" includes antibody fragments having at least 90% or 95% sequence identity to any of the polypeptide sequences disclosed in SEQ ID NOs: 2, 4 6, 8, 12, 14, 16, 18 and 20, including variants modified by mutation to improve the utility thereof (e.g., improved ability to target specific cell types and the like). Such variants include those wherein one or more conservative substitutions are introduced into the heavy chain and/or the light chain of the antibody.

Such variants include those wherein one or more substitutions are introduced into the heavy chain nucleotide sequence and/or the light chain nucleotide sequence of the antibody. In some embodiments the variant has a light chain and/or heavy chain having a nucleotide sequence at least 80% or at least 90% or at least 95% identical to any of the nucleotide sequences set forth in SEQ ID NOs: 1, 3, 5, 7, 11, 13, 15, 17 and 19.

Polynucleotide sequences which code structural features of the antibodies of the invention include those whose sequences are set forth below. Each polynucleotide sequence is followed by the amino acid sequence of the encoded polypeptide. The light chain sequences which are considered to be "corresponding" to heavy chain sequences are those listed as being for the same antibody; i.e., the F2 heavy chain sequences correspond to the F2 light chain sequences, the D10 heavy chain sequences correspond to the D10 light chain sequences, and so forth.

```
SEQ ID NO: 1 4A5 Mouse Anti-ROR1 mAb Heavy Chain
Variable Region Coding Sequence:
GAAGTGAAACTGGTGGAGTCTGGGGGAGGCTTAGTGAAGCCTGGAGGGTC
CCTGAAACTCTCCTGTGCAGCCTCTGGATT
CACTTTCAGTAGCTATGCCATGTCTGGGTTCGCCAGATTCCAGAGAAGA
GGCTGGAGTGGGTCGCATCCATTAGTCGTG
GTGGTACCACCTACTATCCAGACAGTGTGAAGGGCCGATTCACCATCTCC
AGAGATAATGTCAGGAACATCCTGTACCTG
CAAATGAGCAGTCTGAGGTCTGAGGACACGGCCATGTATTACTGTGGAAG
ATATGATTACGACGGGTACTATGCAATGGA
CTACTGGGGTCAAGGAACCTCAGTCACCGTCTCCTCA SEQ ID NO: 2 4A5 Mouse Anti-ROR1 mAb Heavy Chain
Variable Region Polypeptide Sequence:
EVKLVESGGGLVKPGGSLKLSCAASGFTFSSYAMSWVRQIPEKRLEWVAS
ISRGGTTYYPDSVKGRFTISRDNVRNILYL
QMSSLRSEDTAMYYCGRYDYDGYYAMDYWGQGTSVTVSS SEQ ID NO: 3 4A5 Mouse Anti-ROR1 mAb Light Chain
Variable Region Coding Sequence:
GACATCAAGATGACCCAGTCTCCATCTTCCATGTATGCATCTCTAGGAGA
GAGAGTCACTATCACTTGCAAGGCGAGTCC
GGACATTAATAGCTATTTAAGCTGGTTCCAGCAGAAACCAGGGAAATCTC
CTAAGACCCTGATCTATCGTGCAAACAGAT
TGGTTGATGGGGTCCCATCAAGGTTCAGTGGCGGTGGATCTGGGCAAGAT
TATTCTCTCACCATCAACAGCCTGGAGTAT
GAAGATATGGGAATTTATTATTGTCTACAGTATGATGAATTTCCGTACAC
GTTCGGAGGGGGGACCAAGCTGGAAATGAA
AC SEQ ID NO: 4 4A5 Mouse Anti-ROR1 mAb Light Chain
Variable Region Polypeptide Sequence:
DIKMTQSPSSMYASLGERVTITCKASPDINSYLSWFQQKPGKSPKTLIYR
ANRLVDGVPSRFSGGGSGQDYSLTINSLEY
EDMGIYYCLQYDEFPYTFGGGTKLEMK SEQ ID NO: 5 F2, F12 and G6 Mouse Anti-ROR1 mAb
Heavy Chain Variable Region Coding Sequence:
GAGGTCCAGCTACAGCAGTCTGGACCTGAGCTGGAGAAGCCTGGCGCTTC
AGTGAAGATATCCTGCAAGGCTTCTGGTTT
CGCATTCACTGGCTACAACATGAACTGGGTGAAACAGACCAATGGAAAGA
GCCTTGAGTGGATTGGAAGTATTGATCCTT
ACTATGGTGGTTCTACCTACAACCAGAAGTTCAAGGACAAGGCCACATTG
ACTGTAGACAAATCCTCCAGCACAGCCTAC
ATGCAACTCAAGAGCCTCACATCTGATGACTCTGCAGTCTATTACTGTGC
AAGATCCCCGGGGGGGACTATGCTATGGA
CTACTGGGGTCAAGGAACCTCAGTCACCGTCTCCTCA SEQ ID NO: 6 F2, F12 and G6 Mouse Anti-ROR1 mAb
Heavy Chain Variable Region Polypeptide Sequence:
EVQLQQSGPELEKPGASVKISCKASGFAFTGYNMNWVKQTNGKSLEWIGS
IDPYYGGSTYNQKFKDKATLTVDKSSSTAY
MQLKSLTSDDSAVYYCARSPGGDYAMDYWGQGTSVTVSS SEQ ID NO: 7 F2, F12 and G6 Mouse Anti-ROR1 mAb
Light Chain Variable Region Coding Sequence:
GACATCAAGATGACCCAGTCTCCATCTTCCATGTATGCATCTGTAGGAGA
GAGAGTCACTATCACTTGTAAGGCGAGTCA
GGGCATTAATAGCTATTCAGGCTGGTTCCAGCAGAAACCAGGGAAATCTC
CTAAGACCCTGATTTATCGTGGAAATAGAT
TGGTGGATGGGGTCCCATCAAGGTTCAGTGGCAGTGGATCTGGGCAAGAT
TATTCTCTCACCATCAGCAGCCTGGAGTAT
GAAGATATGGGAATTTATTATTGTCTACAGTATGATGAGTTTCCGTACAC
GTTCGGAGGGGGGACCAAGCTGGAAATAAA
AC SEQ ID NOs: 8 F2, F12 and G6 Mouse Anti-ROR1 mAb
Light Chain Variable Region Polypeptide Sequence:
DIKMTQSPSSMYASVGERVTITCKASQGINSYSGWFQQKPGKSPKTLIYR
GNRLVDGVPSRFSGSGSGQDYSLTISSLEY
EDMGIYYCLQYDEFPYTFGGGTKLEIK SEQ ID NO: 9 G3 Mouse Anti-ROR1 mAb Heavy Chain
Variable Region Coding Sequence:
CAGGTCCAACTGCAGCAGCCTGGGGCTGAGCTTGTGAAGCCTGGGACTTC
AGTGAAGCTGTCCTGCAAGGCTTCTGGCTA
CAACTTCACCAACTACTGGATAAACTGGGTGAAGCTGAGGCCTGGACAAG
GCCTTGAGTGGATTGGAGAAATTTATCCTG
GTAGTGGTAGTACTAATTACAATGAGAAGTTCAAGAGCAAGGCCACACTG
ACTGCAGACACATCCTCCAGCACAGCCTAC
ATGCAACTCAGCAGCCTGGCATCTGAAGACTCTGCTCTCTATTACTGTGC
AAGAGATGGTAACTACTATGCTATGGACTA
CTGGGGTCAAGGAACCTCAGTCACCGTCTCCTCA SEQ ID NO: 10 G3 Mouse Anti-ROR1 mAb Heavy Chain
Variable Region Polypeptide Sequence:
QVQLQQPGAELVKPGTSVKLSCKASGYNFTNYWINWVKLRPGQGLEWIGE
IYPGSGSTNYNEKFKSKATLTADTSSSTAY
MQLSSLASEDSALYYCARDGNYYAMDYWGQGTSVTVSS
```

-continued

SEQ ID NO: 11 G3 Mouse Anti-ROR1 mAb Light Chain
Variable Region Coding Sequence:
GATATCCAGATGACACAGACTACATCCTCCCTGTCTGCCTCTCTGGGAGA
CAGAGTCACCATCACTTGCAGGGCAAGTCA
GGACATTAACAATTATTTAAACTGGTATCAACAGAAACCAGATGGAACTG
TTAAACTCCTGATCTACTACACATCAGCAT
TACACTCAGGAGTCCCATCAAGGTTCAGTGGCAGTGGGTCTGGAACAGAT
TATTCTCTCACCATTAGCAACCTGGAACAA
GAAGATATTGCCACTTACTTTTGCCAACAGGGTAATACGCTTCCTCCGTA
CACGTTCGGAGGGGGGACCAAGCTGGAAAT
AAAAC SEQ ID NO: 12 G3 Mouse Anti-ROR1 mAb Light Chain
Variable Region Polypeptide Sequence:
DIQMTQTTSSLSASLGDRVTITCRASQDINNYLNWYQQKPDGTVKLLIYY
TSALHSGVPSRFSGSGSGTDYSLTISNLEQ
EDIATYFCQQGNTLPPYTFGGGTKLEIK SEQ ID NO: 13 D10 Mouse Anti-ROR1 mAb Heavy Chain
Variable Region Coding Sequence:
CAGGTGCAGCTGAAGGAGTCAGGACCTGGCCTGGTGGCGCCCTCACAGAC
TCTGTCCATCACTTGCACTGTCTCTGGGTT
TTCATTAACCAGTTATGGTGTACACTGGGTTCGCCAGCCTCCAGGAAAGG
GTCTGGAGTGGCTGGGAGTAATATGGGCTG
GTGGATTCACAAATTATAATTCGGCTCTCAAGTCCAGACTGAGCATCAGC
AAAGACAACTCCAAGAGCCAAGTTCTCTTA
AAAATGACCAGTCTGCAAACTGATGACACAGCCATGTACTACTGTGCCAG
GAGAGGTAGTTCCTATTCTATGGACTATTG
GGGTCAAGGAACCTCAGTCACCGTCTCCTCA SEQ ID NO: 14 D10 Mouse Anti-ROR1 mAb Heavy Chain
Variable Region Polypeptide Sequence
QVQLKESGPGLVAPSQTLSITCTVSGFSLTSYGVHWVRQPPGKGLEWLGV
IWAGGFTNYNSALKSRLSISKDNSKSQVLL
KMTSLQTDDTAMYYCARRGSSYSMDYWGQGTSVTVSS SEQ ID NO: 15 D10 Mouse Anti-ROR1 mAb Light Chain
Variable Region Coding Sequence:
GAAATTGTGCTCTCTCAGTCTCCAGCCATCACAGCTGCATCTCTGGGCCA
AAAGGTCACCATCACCTGCAGTGCCAGTTC
AAATGTAAGTTACATCCACTGGTACCAGCAGAGGTCAGGCACCTCCCCCA
GACCATGGATTTATGAAATATCCAAACTGG
CTTCTGGAGTCCCAGTTCGCTTCAGTGGCAGTGGGTCTGGGACCTCTTAC
TCTCTCACAATCAGCAGCATGGAGGCTGAA
GATGCTGCCATTTATTATTGTCAGCAGTGGAATTATCCTCTTATCACGTT
CGGCTCGGGGACAAAGTTGGAAATACAA SEQ ID NO: 16 D10 Mouse Anti-ROR1 mAb Light Chain
Variable Region Polypeptide Sequence:
EIVLSQSPAITAASLGQKVTITCSASSNVSYIHWYQQRSGTSPRPWIYEI
SKLASGVPVRFSGSGSGTSYSLTISSMEAE
DAAIYYCQQWNYPLITFGSGTKLEIQ SEQ ID NO: 17 H10 and G11 Mouse Anti-ROR1 mAb
Heavy Chain Variable Region Coding Sequence:
GAAGTGAAGCTGGTGGAGTCTGGGGGAGGCTTAGTGAAGCCTGGAGGGTC
CCTGAAACTCTCCTGTGCAGCCTCTGGATT
CACTTTCAGTAGCTATGCCATGTCTGGGTTCGCCAGACTCCAGAGAAGA
GGCTGGAGTGGGTCGCTTCCATTAGTACTG
GTGCTAGCGCCTACTTTCCAGACAGTGTGAAGGGCCGATTCACCATCTCC
AGAGATAATGCCAGGAACATCCTGTACCTG
CAAATGAGCAGTCTGAGGTCTGAGGACACGGCCATGTATTATTGTGCAAG
GATTACTACGTCTACCTGGTACTTCGATGT
CTGGGGCGCAGGGACCACGGTCACCGTCTCCTCA SEQ ID NO: 18 H10 and G11 Mouse Anti-ROR1 mAb
Heavy Chain Variable Region Polypeptide Sequence:
EVKLVESGGGLVKPGGSLKLSCAASGFTFSSYAMSWVRQTPEKRLEWVAS
ISTGASAYFPDSVKGRFTISRDNARNILYL
QMSSLRSEDTAMYYCARITTSTWYFDVWGAGTIVIVSS SEQ ID NO: 19 H10 and G11 Mouse Anti-ROR1 mAb
Light Chain Variable Region Coding Sequence:
GACATCAAGATGACCCAGTCTCCATCTTCCATGTATGCATCTCTAGGAGA
GAGAGTCACTATCACTTGCAAGGCGAGTCA
GGACATTAATAGTTATTTAAGCTGGTTCCAGCAGAAACCAGGGAAATCTC
CTAAGACCCTGATCTATCGTGCAAACAGAT
TGGTAGATGGGGTCCCATCAAGGTTCAGTGGCAGTGGATCTGGGCAAGAT
TATTCTCTCACCATCAGCAGCCTGGAGTAT
GAAGATATGGGAATTTATTATTGTCTACAGTATGATGAGTTTCCGTACAC
GTTCGGAGGGGGGACCAAGCTGGAAATAAA
AC SEQ ID NO: 20 H10 and G11 Mouse Anti-ROR1 mAb
Light Chain Variable Region Polypeptide Sequence:
DIKMTQSPSSMYASLGERVTITCKASQDINSYLSWFQQKPGKSPKTLIYR
ANRLVDGVPSRFSGSGSGQDYSLTISSLEY
EDMGIYYCLQYDEFPYTFGGGTKLEIK In one aspect, antibodies are provided in which a heavy chain encoded by the polynucleotide sequence of SEQ ID NO:13 and a light chain encoded by the polynucleotide sequence of SEQ ID NO:15.

In another aspect, an antibody of the present invention contains a heavy chain encoded by the polynucleotide sequence of SEQ ID NO:1 and a light chain encoded by the polynucleotide sequence of SEQ ID NO:3.

In further aspects, antibodies are provided which have a heavy chain encoded by the polynucleotide sequence of SEQ ID NO: 5 and a light chain encoded by the polynucleotide sequence of SEQ ID NO: 7; or by the polynucleotide sequence of SEQ ID NO: 9 and a light chain encoded by the polynucleotide sequence of SEQ ID NO: 11; or by the polynucleotide sequence of SEQ ID NO: 15 and a light chain encoded by the polynucleotide sequence of SEQ ID NO: 17.

In another aspect, antibodies are provided which contain a heavy chain with the polypepetide sequence of SEQ ID NO:14 and a light chain with the polypeptide sequence of SEQ ID NO:16.

In another aspect, antibodies are provided which contain a heavy chain with the polypeptide sequence of SEQ ID NO:2 and a light chain with the polypeptide sequence of SEQ ID NO:4.

In one embodiment, isolated polynucleotides which encode an antibody that specifically binds ROR1 protein are provided which are (a) comprised of a heavy chain region coded by polynucleotides having at least 90% sequence identity with any of the sequences selected from the group consisting of SEQ ID NOs: 1, 5, 9, 13 or 17, (b) comprised of a corresponding light chain region encoded by polynucleotides having at least 90% sequence identity with any of the sequences selected from the group consisting of SEQ ID NOs: 3, 7, 11, 15 or 19, and (c) specifically binds either the 3' end or middle portion of the Ig-like region of the extracellular domain of human or murine ROR-1 protein.

Also provided are antibodies which bind residues within the middle of the Ig-like region of the extracellular domain of human or murine ROR-1 protein (amino acids 1-147 in the human molecule). In one aspect, the antibodies of the present invention bind to amino acids 70-130 of human ROR1. Examples of such antibodies include 4A5, G11, H10 and G3.

Alternatively or additionally, a residue corresponding to the one found in the extracellular domain of human ROR-1 protein at position 111 is critical to the binding activity of the antibodies.

Further provided are antibodies that bind residues within the 3' Ig-like region and the linker region between the Ig-like domain and the CRD domain of human or murine ROR-1 protein (amino acids 1-165 in the human molecule). In one aspect, the antibodies of the present invention bind to amino acids 130-165 of human ROR1. Examples of such antibodies include D10, F2, F12 and G6.

Alternatively or additionally, the antibodies bind a glutamic acid residue corresponding to the one found in the extracellular domain of human ROR-1 protein at position 138.

Alternatively or additionally, a residue corresponding to the one found in the extracellular domain of human ROR-1 protein at position 138 is critical to the binding activity of the antibodies.

Alternatively or additionally, the encoded antibody has in vivo activity in reducing leukemic or lymphomic cell burden in an art-accepted animal model at a rate of 2-8 times, or at least 2, 3, 4, 5, 6, 7, or 8 times, that of wild-type human anti-ROR1 antibody or monoclonal 4A5 antibody (disclosed herein).

Alternatively or additionally, the encoded antibody has in vivo activity in inhibiting $CD5^{dull}B220^+$ and $ROR1^{bright}B220^+$ leukemic B cell expansion.

Alternatively or additionally, the encoded antibody is internalized into leukemic or lymphomic cells at a rate of at least 2 times, or at least 2, 3, 4, 5, 6, 7, 8, 9 or 10 times that of monoclonal antibody 4A5. Such antibodies are particularly useful as carriers for drug delivery into a targeted cell.

An example of an antibody possessing all of the a fore-mentioned functional characteristics is D10, which has a heavy chain region encoded by SEQ ID NO: 13 and a light chain region encoded by SEQ ID NO: 15.

In another aspect, polypeptides are provided which consist of or comprise antibodies which specifically bind ROR1 protein and are (a) comprised of a heavy chain region having at least 90% sequence identity with any of the sequences of SEQ. ID. NOs: 2, 6, 10, 14 or 18, (b) comprised of a corresponding light chain region having at least 90% sequence identity with any of the sequences of SEQ ID NOs: 4, 8, 12, 16 or 20, and (c) specifically binds either the 3' end or middle portion of the Ig-like region of the extracellular domain of human or murine ROR-1 protein. In one aspect, the isolated polypeptide is an antibody. In a further aspect, the polypeptide is a Fab or F(ab)'2.

In certain embodiments, an antibody of the present invention may further contain a detectable label. Such labels are known in the art and include radio-isotopes and fluorescent labels. As such, internalization of a compound evidencing passage through transporters can be detected by detecting a signal from within a cell from any of a variety of reporters. The reporter can be a label such as a fluorophore, a chromophore, a radioisotope. Confocal imagining can also be used to detect internalization of a label as it provides sufficient spatial resolution to distinguish between fluorescence on a cell surface and fluorescence within a cell; alternatively, confocal imaging can be used to track the movement of compounds over time. In another approach, internalization of a compound is detected using a reporter that is a substrate for an enzyme expressed within a cell. Once the complex is internalized, the substrate is metabolized by the enzyme and generates an optical signal or radioactive decay that is indicative of uptake. Light emission can be monitored by commercial PMT-based instruments or by CCD-based imaging systems. In addition, assay methods utilizing LCMS detection of the transported compounds or electrophysiological signals indicative of transport activity are also employed.

In certain therapeutic embodiments, the selected antibody may be administered alone, in combination with another antibody of the invention, or with one or more combinatorial therapeutic agents to treat an ROR-1 cancer. When one or more the antibodies described herein are administered as therapeutic agents, they may exert a beneficial effect in the subject by a variety of mechanisms. For example, in certain embodiments, antibodies that specifically bind ROR1 are purified and administered to a patient to neutralize one or more forms of ROR1, to block one or more activities of ROR1, or to block or inhibit an interaction of one or more forms of ROR1 with another biomolecule; e.g., to treat CLL or other ROR1 cancers. All such therapeutic methods are practiced by delivery of a therapeutically effective dosage of a pharmaceutical composition containing the therapeutic antibodies and agents, which can be determined by a pharmacologist or clinician of ordinary skill in human cancer immunotherapy.

In one embodiment, the present invention provides for a method for of treating cancer by the administration to a human subject in need thereof of a therapeutically effective dose of an antibody according to the invention.

In another embodiment, the present invention provides a method for of treating cancer comprising administration to a human subject in need thereof of a therapeutically effective dose of an antibody according to the invention.

Advantageously, the methods of the invention provide for reduction of leukemic or lymphomic cell burden (as demonstrated in and equivalent to an art-accepted animal model) of 2-8 times, or at least 2, 3, 4, 5, 6, 7, or 8 times, that of wild-type human anti-ROR1 antibody or monoclonal 4A5 antibody (disclosed herein).

The methods of the invention further provide a therapeutic approach to inhibiting $CD5^{dull}B220^+$ and $ROR1^{bright}B220^+$ leukemic B cell expansion.

As discussed herein, the antibodies of the invention may include humanized antibodies, and can be combined for therapeutic use with additional active or inert ingredients, e.g., in conventional pharmaceutically acceptable carriers or diluents, e.g., immunogenic adjuvants, and optionally with adjunctive or combinatorially active molecules such as anti-inflammatory and anti-fibrinolytic drugs. Antibodies which readily internalize into cells as demonstrated herein with respect to the D10 antibody are also of particular use as carriers for drug delivery into target cells (for example, as shown in FIGS. 21-23). Those of ordinary skill in the art will be familiar with methods for producing antibody-drug conjugates useful in such drug delivery protocols.

In carrying out various assay, diagnostic, and therapeutic methods of the invention, it is desirable to prepare in advance kits comprises a combination of antibodies as described herein with other materials. For example, in the case of sandwich enzyme immunoassays, kits of the invention may contain an antibody that specifically binds ROR1 optionally linked to an appropriate carrier, a freeze-dried preparation or a solution of an enzyme-labeled monoclonal antibody which can bind to the same antigen together with the monoclonal antibody or of a polyclonal antibody labeled with the enzyme in the same manner, a standard solution of purified ROR1, a buffer solution, a washing solution, pipettes, a reaction container and the like. In addition, the kits optionally include labeling and/or instructional materials providing directions (i.e., protocols) for the practice of the methods described herein in an assay environment. While the instructional materials typically comprise written or printed materials, they are not limited to such. Any medium capable of storing such instructions and communicating them to an end user is contemplated. Such media include, but are not limited to electronic storage media (e.g., magnetic discs, tapes, cartridges, chips), optical media (e.g., CD ROM), and the like. Such media may include addresses to internet sites that provide such instructional materials.

In general, an in vitro method of diagnosing a ROR-1 cancer will comprise contacting putative cancer cells from a human subject with an antibody according to the invention, and detecting binding with ROR-1 expressed on said cells as compared to expression on post-embryonic human noncancer cells. All such diagnostic methods are practiced by delivery of a diagnostically effect quantity of antibodies according to the invention, which can be determined by a diagnostician or in vitro diagnostic engineer of ordinary skill in human cancer diagnosis.

The following examples are intended to illustrate but not limit the invention.

Example 1: Generation of Monoclonal Anti-ROR1 Antibodies

For the production of the hybridoma-generated mAbs, mice were inoculated with DNA, protein and adenoviral constructs that express the extracellular portion (AA 1-406) of the ROR1 protein that include the Ig-like, CRD and Kringle domains and adjacent linker regions (FIGS. 10-11). Because of the high degree of homology between the murine and human molecules, a variety of cytokines and immune stimulatory agents, such as Freund's Complete Adjuvant, were co-injected to maximize the generation of anti-human ROR1 antibodies. Hybridoma-generated mAbs were generated and screened for binding to human and murine ROR1. An example of hybridoma derived mAbs is D10.

Example 2: Generation of Anti-ROR1 Antibodies Using Phage Display

A second set of antibodies was generated through the use of a proprietary enhanced phage library (Alere, Inc. San Diego). These anti-human ROR1 antibodies bind epitopes that span the entire length of the extra-cellular domain of the ROR1 protein (FIG. 12). An example of a phage display derived anti-ROR1 antibody is 4A5.

Example 3: In Vitro Analysis of Anti-ROR1 Antibodies

Antibodies generated through either hybridomas or phage display were screened for binding to human and murine ROR1. It was determined that the anti-ROR1 antibodies D10 and 4A5 bound only to human ROR1 and did not cross react with murine ROR1.

Example 4: Determination of Binding Sites for Anti-ROR1 Antibodies

Because the anti-ROR1 mAbs are species specific, a series of chimeric proteins were generated that were used to determine the binding site for each of the anti-ROR1 mAbs (FIG. 13). As a second level screen, a series of deletion constructs were generated to determine the actual extracellular ROR1 domain to which the mAbs bind. Once the binding domain was identified, truncated chimeric ROR1 molecules to identify specific sub-regions were generated that are recognized by the anti-human ROR1 mAbs (FIG. 14). As a final step, the actual amino acids targeted by these antibodies were determined. For this final screen, murinized human amino acids in the sub-domain fragments were generated to determine critical residues required for mAb binding (FIG. 15). From this screening paradigm, the binding sub-domains for the mAbs were determined (FIG. 15). It was determine that the D10 anti-human ROR1 mAb required the glutamic acid residue at position 138 for binding to the Ig-like domain of the human ROR1 molecule. When this amino acid is replaced with the murine molecule's lysine residue, the D10 molecule no longer bound to the ROR1 protein.

In a similar manner, it was determined that 4A5 anti-human ROR1 mAb required the isoleucine residue at position 111 for binding to human ROR1 molecule (FIG. 24). When this amino acid is replaced with the murine molecule's asparagine residue, the 4A5 molecule no longer bound to the ROR1 protein. It was also determined that the anti-ROR1 antibodies G11, H10 and G3 bind the same region as 4A5.

Using standard cross blocking techniques the binding sites for anti-ROR1 antibodies F2, F12 and G6 were determined. These experiments determined that antibodies F2, F12 and G6 cross block the anti-ROR1 antibody D10, indicating that they share a binding site.

Example 5: Determination of the $K_D$ Values for the Anti-ROR1 Antibodies D10 and 4A5

The $K_D$ values for the anti-ROR1 antibodies was determined using standard techniques. It was determined that the $K_D$ for the D10 antibody was 40 nM and for the antibody 4A5 was 4 nM (FIGS. 16A-16B).

Example 6: In Vivo Analysis of Anti-ROR1 Antibodies

The D10 mAb was assessed in several in vivo models. In a murine in vivo xenograph, niche-dependent, activity model two doses of the mAb were administered at 10 mg/kg against 4 primary patient CLL cells in 76 mice. As shown in FIG. 17, D10 mAb substantially eliminated patient CLL cells in a dose dependent manner. In contrast, the 4A5 mAb had minimal activity in these studies even though the kDa of this mAb is 10 fold greater (4 vs. 40) for the D10 mAb.

In addition to this activity model, the D10 mAb was also tested in an immune competent transgenic mouse model that spontaneously generates leukemic cells expressing the human ROR1 protein (FIGS. 18-20). The ROR1-specific mAbs D10 and 4A5 or control IgG antibodies (10 mg/kg) were administered before and after adoptive transfer of ROR1×TCL1 CLL B cells into Balb C mice. The D10 mAb, but not control IgG or 4A5, was able to inhibit the development and expansion of the ROR1×TCL1 leukemic B cells in the blood of recipient animals until two weeks after receiving the last infusion of MAb.

Along with the anti-leukemic activity of this mAb, it has also been shown that the D10 anti-ROR1 antibody is internalized into patient CLL cells and B cell leukemia and lymphoma cell lines at a greater rate and degree than other anti-ROR1 MAbs that bind other antigenic sites on the extracellular portion of the ROR1 protein (FIGS. 21-23). Because of the absence of the ROR1 protein on post-partum tissues and its rapid rate of internalization, the D10 mAb may serve as an excellent carrier protein for drugs; for example, for use in directed antibody-drug conjugate (ADC) mediated cytotoxicity. Based on these preclinical findings, the D10 mAb has potential to have therapeutic activity against ROR1 expressing leukemias, lymphomas and solid tumor cancers as a targeted therapy and/or conjugated drug carrier.

Although the foregoing subject matter has been described in some detail by way of illustration and example for purposes of clarity of understanding, it will be understood by those skilled in the art that certain changes and modifications can be practiced within the scope of the appended claims.

What is claimed is:

1. A method of identifying an anti-ROR1 antibody, the method comprising:
   (i) contacting an antibody with a first ROR1 polypeptide comprising amino acid residues 1-147 of SEQ ID NO:36;
   (ii) detecting said antibody binding to said first ROR1 polypeptide;
   (iii) contacting said antibody with a second ROR 1 polypeptide comprising amino acid residues 1-147 of SEQ ID NO:37 or amino acid residues 1-147 of SEQ ID NO:36, wherein the glutamic acid residue at position 138 of SEQ ID NO:36 is replaced by lysine; and
   (iv) detecting said antibody not binding to said second ROR1 polypeptide, thereby identifying an anti-ROR1 antibody.

2. The method of claim 1, wherein said first ROR1 polypeptide is a truncated ROR1 polypeptide.

3. The method of claim 2, wherein said truncated ROR1 polypeptide comprises amino acid residues 1-165 of SEQ ID NO:36.

4. The method of claim 1, wherein said second ROR1 polypeptide is a truncated ROR1 polypeptide.

5. The method of claim 4, wherein said truncated ROR1 polypeptide comprises amino acid residues 1-165 of SEQ ID NO:37.

6. The method of claim 1, wherein said antibody is a humanized antibody.

7. The method of claim 1, wherein said antibody is an antibody fragment.

8. The method of claim 1, wherein said antibody is a chimeric antibody.

9. The method of claim 1, wherein said antibody is a single chain antibody.

10. The method of claim 1, wherein said antibody binds to said first ROR1 polypeptide with a $K_D$ of less than 40 nM.

11. The method of claim 1, wherein said antibody binds to said first ROR1 polypeptide with a $K_D$ of about 40 nM.

* * * * *

SEQUENCE LISTING

<160> NUMBER OF SEQ ID NOS: 37

<210> SEQ ID NO 1
<211> LENGTH: 357
<212> TYPE: DNA
<213> ORGANISM: Mus musculus

<400> SEQUENCE: 1
gaagtgaaac tggtggagtc tgggggaggc ttagtgaagc ctggagggtc cctgaaactc      60
tcctgtgcag cctctggatt cactttcagt agctatgcca tgtcttgggt tcgccagatt     120
ccagagaaga ggctggagtg ggtcgcatcc attagtcgtg gtggtaccac ctactatcca     180
gacagtgtga agggccgatt caccatctcc agagataatg tcaggaacat cctgtacctg     240
caaatgagca gtctgaggtc tgaggacacg gccatgtatt actgtggaag atatgattac     300
gacgggtact atgcaatgga ctactggggt caaggaacct cagtcaccgt ctcctca        357

<210> SEQ ID NO 2
<211> LENGTH: 119
<212> TYPE: PRT
<213> ORGANISM: Mus musculus

<400> SEQUENCE: 2

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Ile Pro Glu Lys Arg Leu Glu Trp Val
        35                  40                  45

Ala Ser Ile Ser Arg Gly Gly Thr Thr Tyr Tyr Pro Asp Ser Val Lys
    50                  55                  60

Gly Arg Phe Thr Ile Ser Arg Asp Asn Val Arg Asn Ile Leu Tyr Leu
65                  70                  75                  80

Gln Met Ser Ser Leu Arg Ser Glu Asp Thr Ala Met Tyr Tyr Cys Gly
                85                  90                  95

Arg Tyr Asp Tyr Asp Gly Tyr Tyr Ala Met Asp Tyr Trp Gly Gln Gly
            100                 105                 110

Thr Ser Val Thr Val Ser Ser
        115

<210> SEQ ID NO 3
<211> LENGTH: 322
<212> TYPE: DNA
<213> ORGANISM: Mus musculus

<400> SEQUENCE: 3
gacatcaaga tgacccagtc tccatcttcc atgtatgcat ctctaggaga gagagtcact      60
atcacttgca aggcgagtcc ggacattaat agctatttaa gctggttcca gcagaaacca     120
gggaaatctc ctaagaccct gatctatcgt gcaaacagat tggttgatgg ggtcccatca     180
aggttcagtg gcggtggatc tgggcaagat tattctctca ccatcaacag cctggagtat     240
gaagatatgg gaatttatta ttgtctacag tatgatgaat tccgtacacg ttcggaggg      300 gggaccaagc tggaaatgaa ac                                              322

<210> SEQ ID NO 4
<211> LENGTH: 107
<212> TYPE: PRT
<213> ORGANISM: Mus musculus

<400> SEQUENCE: 4

Asp Ile Lys Met Thr Gln Ser Pro Ser Ser Met Tyr Ala Ser Leu Gly
1               5                   10                  15

Glu Arg Val Thr Ile Thr Cys Lys Ala Ser Pro Asp Ile Asn Ser Tyr
            20                  25                  30

Leu Ser Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
50                  55                  60

Gly Gly Ser Gly Gln Asp Tyr Ser Leu Thr Ile Asn Ser Leu Glu Tyr
65                  70                  75                  80

Glu Asp Met Gly Ile Tyr Tyr Cys Leu Gln Tyr Asp Glu Phe Pro Tyr
                85                  90                  95

Thr Phe Gly Gly Gly Thr Lys Leu Glu Met Lys
            100                 105

<210> SEQ ID NO 5
<211> LENGTH: 357
<212> TYPE: DNA
<213> ORGANISM: Mus musculus

<400> SEQUENCE: 5
gaggtccagc tacagcagtc tggacctgag ctggagaagc ctggcgcttc agtgaagata     60
tcctgcaagg cttctggttt cgcattcact ggctacaaca tgaactgggt gaaacagacc    120
aatggaaaga gccttgagtg gattggaagt attgatcctt actatggtgg ttctacctac    180
aaccagaagt tcaaggacaa ggccacattg actgtagaca atcctccag cacagcctac     240 atgcaactca gagcctcac atctgatgac tctgcagtct attactgtgc aagatccccg     300 ggggggact atgctatgga ctactgggt caaggaacct cagtcaccgt ctcctca        357

<210> SEQ ID NO 6
<211> LENGTH: 119
<212> TYPE: PRT
<213> ORGANISM: Mus musculus

<400> SEQUENCE: 6

Glu Val Gln Leu Gln Gln Ser Gly Pro Glu Leu Glu Lys Pro Gly Ala
1               5                   10                  15

Ser Val Lys Ile Ser Cys Lys Ala Ser Gly Phe Ala Phe Thr Gly Tyr
            20                  25                  30

Asn Met Asn Trp Val Lys Gln Thr Asn Gly Lys Ser Leu Glu Trp Ile
        35                  40                  45

Gly Ser Ile Asp Pro Tyr Tyr Gly Gly Ser Thr Tyr Asn Gln Lys Phe
50                  55                  60

Lys Asp Lys Ala Thr Leu Thr Val Asp Lys Ser Ser Thr Ala Tyr
65                  70                  75                  80

Met Gln Leu Lys Ser Leu Thr Ser Asp Asp Ser Ala Val Tyr Tyr Cys
                85                  90                  95

Ala Arg Ser Pro Gly Gly Asp Tyr Ala Met Asp Tyr Trp Gly Gln Gly
            100                 105                 110

Thr Ser Val Thr Val Ser Ser
        115

<210> SEQ ID NO 7
<211> LENGTH: 322

<212> TYPE: DNA
<213> ORGANISM: Mus musculus

<400> SEQUENCE: 7

```
gacatcaaga tgacccagtc tccatcttcc atgtatgcat ctgtaggaga gagagtcact    60
atcacttgta aggcgagtca gggcattaat agctattcag ctggttcca gcagaaacca    120
gggaaatctc ctaagaccct gatttatcgt ggaaatagat tggtggatgg ggtcccatca   180
aggttcagtg gcagtggatc tgggcaagat tattctctca ccatcagcag cctggagtat    240
gaagatatgg aatttatta ttgtctacag tatgatgagt ttccgtacac gttcggaggg    300
gggaccaagc tggaaataaa ac                                              322
```

<210> SEQ ID NO 8
<211> LENGTH: 107
<212> TYPE: PRT
<213> ORGANISM: Mus musculus

<400> SEQUENCE: 8

Asp Ile Lys Met Thr Gln Ser Pro Ser Ser Met Tyr Ala Ser Val Gly
1               5                   10                  15
Glu Arg Val Thr Ile Thr Cys Lys Ala Ser Gln Gly Ile Asn Ser Tyr
            20                  25                  30
Ser Gly Trp Phe Gln Gln Lys Pro Gly Lys Ser Pro Lys Thr Leu Ile
        35                  40                  45
Tyr Arg Gly Asn Arg Leu Val Asp Gly Val Pro Ser Arg Phe Ser Gly
    50                  55                  60
Ser Gly Ser Gly Gln Asp Tyr Ser Leu Thr Ile Ser Ser Leu Glu Tyr
65                  70                  75                  80
Glu Asp Met Gly Ile Tyr Tyr Cys Leu Gln Tyr Asp Glu Phe Pro Tyr
                85                  90                  95
Thr Phe Gly Gly Gly Thr Lys Leu Glu Ile Lys
            100                 105

<210> SEQ ID NO 9
<211> LENGTH: 354
<212> TYPE: DNA
<213> ORGANISM: Mus musculus

<400> SEQUENCE: 9

```
caggtccaac tgcagcagcc tggggctgag cttgtgaagc ctggggcttc agtgaagctg     60
tcctgcaagg cttctggcta caacttcacc aactactgga taaactgggt gaagctgagg    120
cctggacaag gccttgagtg gattggagaa atttatcctg gtagtggtag tactaattac    180
aatgagaagt tcaagagcaa ggccacactg actgcagaca catcctccag cacagcctac    240
atgcaactca gcagcctggc atctgaagac tctgctctct attactgtgc aagagatggt    300
aactactatg ctatggacta ctggggtcaa ggaacctcag tcaccgtctc ctca           354
```

<210> SEQ ID NO 10
<211> LENGTH: 118
<212> TYPE: PRT
<213> ORGANISM: Mus musculus

<400> SEQUENCE: 10

Gln Val Gln Leu Gln Gln Pro Gly Ala Glu Leu Val Lys Pro Gly Thr
1               5                   10                  15
Ser Val Lys Leu Ser Cys Lys Ala Ser Gly Tyr Asn Phe Thr Asn Tyr
            20                  25                  30

```
Trp Ile Asn Trp Val Lys Leu Arg Pro Gly Gln Gly Leu Glu Trp Ile
            35                  40                  45
Gly Glu Ile Tyr Pro Gly Ser Gly Ser Thr Asn Tyr Asn Glu Lys Phe
        50                  55                  60
Lys Ser Lys Ala Thr Leu Thr Ala Asp Thr Ser Ser Ser Thr Ala Tyr
 65                  70                  75                  80
Met Gln Leu Ser Ser Leu Ala Ser Glu Asp Ser Ala Leu Tyr Tyr Cys
                85                  90                  95
Ala Arg Asp Gly Asn Tyr Tyr Ala Met Asp Tyr Trp Gly Gln Gly Thr
            100                 105                 110
Ser Val Thr Val Ser Ser
            115
```

```
<210> SEQ ID NO 11
<211> LENGTH: 325
<212> TYPE: DNA
<213> ORGANISM: Mus musculus

<400> SEQUENCE: 11
gatatccaga tgacacagac tacatcctcc ctgtctgcct ctctgggaga cagagtcacc      60
atcacttgca gggcaagtca ggacattaac aattatttaa actggtatca acagaaacca     120
gatggaactg ttaaactcct gatctactac acatcagcat acactcagg agtcccatca      180 aggttcagtg gcagtgggtc tggaacagat tattctctca ccattagcaa cctggaacaa    240
gaagatattg ccacttactt ttgccaacag ggtaatacgc ttcctccgta cacgttcgga    300
gggggaccaa gctggaaat aaaac                                            325
```

```
<210> SEQ ID NO 12
<211> LENGTH: 108
<212> TYPE: PRT
<213> ORGANISM: Mus musculus

<400> SEQUENCE: 12

Asp Ile Gln Met Thr Gln Thr Thr Ser Ser Leu Ser Ala Ser Leu Gly
  1               5                  10                  15
Asp Arg Val Thr Ile Thr Cys Arg Ala Ser Gln Asp Ile Asn Asn Tyr
            20                  25                  30
Leu Asn Trp Tyr Gln Gln Lys Pro Asp Gly Thr Val Lys Leu Leu Ile
        35                  40                  45
Tyr Tyr Thr Ser Ala Leu His Ser Gly Val Pro Ser Arg Phe Ser Gly
 50                  55                  60
Ser Gly Ser Gly Thr Asp Tyr Ser Leu Thr Ile Ser Asn Leu Glu Gln
 65                  70                  75                  80
Glu Asp Ile Ala Thr Tyr Phe Cys Gln Gln Gly Asn Thr Leu Pro Pro
                85                  90                  95
Tyr Thr Phe Gly Gly Gly Thr Lys Leu Glu Ile Lys
            100                 105
```

```
<210> SEQ ID NO 13
<211> LENGTH: 351
<212> TYPE: DNA
<213> ORGANISM: Mus musculus

<400> SEQUENCE: 13
caggtgcagc tgaaggagtc aggacctggc ctggtggcgc cctcacagac tctgtccatc      60
acttgcactg tctctgggtt ttcattaacc agttatggtg tacactgggt tcgccagcct    120
```

```
ccaggaaagg gtctggagtg gctgggagta atatgggctg gtggattcac aaattataat    180
tcggctctca agtccagact gagcatcagc aagacaact  ccaagagcca agttctctta    240
aaaatgacca gtctgcaaac tgatgacaca gccatgtact actgtgccag agagggtagt   300
tcctattcta tggactattg gggtcaagga acctcagtca ccgtctcctc a            351
```

<210> SEQ ID NO 14
<211> LENGTH: 117
<212> TYPE: PRT
<213> ORGANISM: Mus musculus

<400> SEQUENCE: 14

Gln Val Gln Leu Lys Glu Ser Gly Pro Gly Leu Val Ala Pro Ser Gln
1               5                   10                  15

Thr Leu Ser Ile Thr Cys Thr Val Ser Gly Phe Ser Leu Thr Ser Tyr
            20                  25                  30

Gly Val His Trp Val Arg Gln Pro Pro Gly Lys Gly Leu Glu Trp Leu
        35                  40                  45

Gly Val Ile Trp Ala Gly Gly Phe Thr Asn Tyr Asn Ser Ala Leu Lys
    50                  55                  60

Ser Arg Leu Ser Ile Ser Lys Asp Asn Ser Lys Ser Gln Val Leu Leu
65                  70                  75                  80

Lys Met Thr Ser Leu Gln Thr Asp Asp Thr Ala Met Tyr Tyr Cys Ala
                85                  90                  95

Arg Arg Gly Ser Ser Tyr Ser Met Asp Tyr Trp Gly Gln Gly Thr Ser
            100                 105                 110

Val Thr Val Ser Ser
        115

<210> SEQ ID NO 15
<211> LENGTH: 318
<212> TYPE: DNA
<213> ORGANISM: Mus musculus

<400> SEQUENCE: 15

```
gaaattgtgc tctctcagtc tccagccatc acagctgcat ctctgggcca aaaggtcacc     60
atcacctgca gtgccagttc aaatgtaagt tacatccact ggtaccagca gaggtcaggc    120
acctccccca gaccatggat ttatgaaata tccaaactgg cttctggagt cccagttcgc    180
ttcagtggca gtgggtctgg gacctcttac tctctcacaa tcagcagcat ggaggctgaa    240
gatgctgcca tttattattg tcagcagtgg aattatcctc ttatcacgtt cggctcgggg    300
acaaagttgg aaatacaa                                                  318
```

<210> SEQ ID NO 16
<211> LENGTH: 106
<212> TYPE: PRT
<213> ORGANISM: Mus musculus

<400> SEQUENCE: 16

Glu Ile Val Leu Ser Gln Ser Pro Ala Ile Thr Ala Ala Ser Leu Gly
1               5                   10                  15

Gln Lys Val Thr Ile Thr Cys Ser Ala Ser Ser Asn Val Ser Tyr Ile
            20                  25                  30

His Trp Tyr Gln Gln Arg Ser Gly Thr Ser Pro Arg Pro Trp Ile Tyr
        35                  40                  45

Glu Ile Ser Lys Leu Ala Ser Gly Val Pro Val Arg Phe Ser Gly Ser

-continued

```
                    50                  55                  60
Gly Ser Gly Thr Ser Tyr Ser Leu Thr Ile Ser Ser Met Glu Ala Glu
 65                  70                  75                  80

Asp Ala Ala Ile Tyr Tyr Cys Gln Gln Trp Asn Tyr Pro Leu Ile Thr
                 85                  90                  95

Phe Gly Ser Gly Thr Lys Leu Glu Ile Gln
            100                 105

<210> SEQ ID NO 17
<211> LENGTH: 354
<212> TYPE: DNA
<213> ORGANISM: Mus musculus

<400> SEQUENCE: 17
gaagtgaagc tggtggagtc tgggggaggc ttagtgaagc ctggagggtc cctgaaactc        60
tcctgtgcag cctctggatt cactttcagt agctatgcca tgtcttgggt tcgccagact       120
ccagagaaga ggctggagtg ggtcgcttcc attagtactg gtgctagcgc ctactttcca       180
gacagtgtga agggccgatt caccatctcc agagataatg ccaggaacat cctgtacctg       240
caaatgagca gtctgaggtc tgaggacacg gccatgtatt attgtgcaag gattactacg       300
tctacctggt acttcgatgt ctggggcgca gggaccacgg tcaccgtctc ctca             354

<210> SEQ ID NO 18
<211> LENGTH: 118
<212> TYPE: PRT
<213> ORGANISM: Mus musculus

<400> SEQUENCE: 18

Glu Val Lys Leu Val Glu Ser Gly Gly Gly Leu Val Lys Pro Gly Gly
  1               5                  10                  15

Ser Leu Lys Leu Ser Cys Ala Ala Ser Gly Phe Thr Phe Ser Ser Tyr
                 20                  25                  30

Ala Met Ser Trp Val Arg Gln Thr Pro Glu Lys Arg Leu Glu Trp Val
             35                  40                  45

Ala Ser Ile Ser Thr Gly Ala Ser Ala Tyr Phe Pro Asp Ser Val Lys
         50                  55                  60

Gly Arg Phe Thr Ile Ser Arg Asp Asn Ala Arg Asn Ile Leu Tyr Leu
 65                  70                  75                  80

Gln Met Ser Ser Leu Arg Ser Glu Asp Thr Ala Met Tyr Tyr Cys Ala
                 85                  90                  95

Arg Ile Thr Thr Ser Thr Trp Tyr Phe Asp Val Trp Gly Ala Gly Thr
            100                 105                 110

Thr Val Thr Val Ser Ser
        115

<210> SEQ ID NO 19
<211> LENGTH: 322
<212> TYPE: DNA
<213> ORGANISM: Mus musculus

<400> SEQUENCE: 19
gacatcaaga tgacccagtc tccatcttcc atgtatgcat ctctaggaga gagagtcact        60
atcacttgca aggcgagtca ggacattaat agttatttaa gctggttcca gcagaaacca       120
gggaaatctc ctaagaccct gatctatcgt gcaaacagat ggtagatgg  ggtcccatca       180 aggttcagtg gcagtggatc tgggcaagat tattctctca ccatcagcag cctggagtat       240
```

```
gaagatatgg gaatttatta ttgtctacag tatgatgagt ttccgtacac gttcggaggg    300
gggaccaagc tggaaataaa ac                                             322
```

<210> SEQ ID NO 20
<211> LENGTH: 107
<212> TYPE: PRT
<213> ORGANISM: Mus musculus

<400> SEQUENCE: 20

```
Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
            20                  25                  30

Leu Ser Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Tyr Ser Leu Thr Ile Ser Ser Leu Glu Tyr
65                  70                  75                  80

Glu Asp Met Gly Ile Tyr Tyr Cys Leu Gln Tyr Asp Glu Phe Pro Tyr
                85                  90                  95

Thr Phe Gly Gly Gly Thr Lys Leu Glu Ile Lys
            100                 105
```

<210> SEQ ID NO 21
<211> LENGTH: 106
<212> TYPE: PRT
<213> ORGANISM: Mus musculus
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (31)..(34)
<223> OTHER INFORMATION: Xaa can be any naturally occurring amino acid
<220> FEATURE:
<221> NAME/KEY: misc_feature
<222> LOCATION: (60)..(62)
<223> OTHER INFORMATION: Xaa can be any naturally occurring amino acid
<220> FEATURE:
<221> NAME/KEY: misc_feature
<222> LOCATION: (73)..(73)
<223> OTHER INFORMATION: Xaa can be any naturally occurring amino acid

<400> SEQUENCE: 21

```
Glu Val Lys Leu Val Glu Ser Gly Gly Xaa Gly Leu Val Lys Pro Gly
1               5                   10                  15

Gly Ser Leu Lys Leu Ser Cys Ala Ala Ser Gly Phe Thr Phe Xaa Xaa
            20                  25                  30

Xaa Xaa Ser Ser Tyr Ala Met Ser Trp Val Arg Gln Ile Pro Glu Lys
        35                  40                  45

Arg Leu Glu Trp Val Ala Ser Ile Ser Arg Gly Xaa Xaa Xaa Gly Thr
    50                  55                  60

Thr Tyr Tyr Pro Asp Ser Val Lys Xaa Gly Arg Phe Thr Ile Ser Arg
65                  70                  75                  80

Asp Asn Val Arg Asn Ile Leu Tyr Leu Gln Met Ser Ser Leu Arg Ser
                85                  90                  95

Glu Asp Thr Ala Met Tyr Tyr Cys Gly Arg
            100                 105
```

```
<210> SEQ ID NO 22
<211> LENGTH: 106
<212> TYPE: PRT
<213> ORGANISM: Mus musculus
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (31)..(34)
<223> OTHER INFORMATION: Xaa can be any naturally occurring amino acid
<220> FEATURE:
<221> NAME/KEY: misc_feature
<222> LOCATION: (60)..(62)
<223> OTHER INFORMATION: Xaa can be any naturally occurring amino acid
<220> FEATURE:
<221> NAME/KEY: misc_feature
<222> LOCATION: (73)..(73)
<223> OTHER INFORMATION: Xaa can be any naturally occurring amino acid

<400> SEQUENCE: 22

Glu Val Lys Leu Val Glu Ser Gly Gly Xaa Gly Leu Val Lys Pro Gly
1               5                   10                  15

Gly Ser Leu Lys Leu Ser Cys Ala Ala Ser Gly Phe Ala Phe Xaa Xaa
                20                  25                  30

Xaa Xaa Ser Ser Tyr Asp Met Ser Trp Val Arg Gln Thr Pro Glu Lys
        35                  40                  45

Arg Leu Glu Trp Val Ala Thr Ile Ser Ser Gly Xaa Xaa Xaa Ser Tyr
50                  55                  60

Thr Tyr Tyr Pro Asp Ser Val Lys Xaa Gly Arg Phe Thr Ile Ser Arg
65                  70                  75                  80

Asp Asn Ala Arg Asn Thr Leu Tyr Leu Gln Met Ser Ser Leu Arg Ser
                85                  90                  95

Glu Asp Thr Ala Leu Tyr Tyr Cys Ala Arg
            100                 105

<210> SEQ ID NO 23
<211> LENGTH: 106
<212> TYPE: PRT
<213> ORGANISM: Homo sapiens
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (31)..(34)
<223> OTHER INFORMATION: Xaa can be any naturally occurring amino acid
<220> FEATURE:
<221> NAME/KEY: misc_feature
<222> LOCATION: (60)..(61)
<223> OTHER INFORMATION: Xaa can be any naturally occurring amino acid
<220> FEATURE:
<221> NAME/KEY: misc_feature
<222> LOCATION: (73)..(73)
<223> OTHER INFORMATION: Xaa can be any naturally occurring amino acid

<400> SEQUENCE: 23

Glu Val Gln Leu Val Glu Ser Gly Gly Xaa Gly Leu Val Gln Pro Gly
1               5                   10                  15

Gly Ser Leu Arg Leu Ser Cys Ala Ala Ser Gly Phe Thr Phe Xaa Xaa
                20                  25                  30

Xaa Xaa Ser Ser Tyr Ser Met Asn Trp Val Arg Gln Ala Pro Gly Lys
        35                  40                  45

Gly Leu Glu Trp Val Ser Tyr Ile Ser Ser Ser Xaa Xaa Ser Ser Thr
50                  55                  60
```

Ile Tyr Tyr Ala Asp Ser Val Lys Xaa Gly Arg Phe Thr Ile Ser Arg
65                  70                  75                  80

Asp Asn Ala Lys Asn Ser Leu Tyr Leu Gln Met Asn Ser Leu Arg Ala
                85                  90                  95

Glu Asp Thr Ala Val Tyr Tyr Cys Ala Arg
            100                 105

<210> SEQ ID NO 24
<211> LENGTH: 106
<212> TYPE: PRT
<213> ORGANISM: Mus musculus
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (31)..(34)
<223> OTHER INFORMATION: Xaa can be any naturally occurring amino acid
<220> FEATURE:
<221> NAME/KEY: misc_feature
<222> LOCATION: (60)..(61)
<223> OTHER INFORMATION: Xaa can be any naturally occurring amino acid
<220> FEATURE:
<221> NAME/KEY: misc_feature
<222> LOCATION: (73)..(73)
<223> OTHER INFORMATION: Xaa can be any naturally occurring amino acid

<400> SEQUENCE: 24

Glu Val Gln Leu Gln Gln Ser Gly Pro Xaa Glu Leu Glu Lys Pro Gly
1               5                   10                  15

Ala Ser Val Lys Ile Ser Cys Lys Ala Ser Gly Phe Ala Phe Xaa Xaa
                20                  25                  30

Xaa Xaa Thr Gly Tyr Asn Met Asn Trp Val Lys Gln Thr Asn Gly Lys
            35                  40                  45

Ser Leu Glu Trp Ile Gly Ser Ile Asp Pro Tyr Xaa Xaa Tyr Gly Gly
        50                  55                  60

Ser Thr Tyr Asn Gln Lys Phe Lys Xaa Asp Lys Ala Thr Leu Thr Val
65                  70                  75                  80

Asp Lys Ser Ser Ser Thr Ala Tyr Met Gln Leu Lys Ser Leu Thr Ser
                85                  90                  95

Asp Asp Ser Ala Val Tyr Tyr Cys Ala Arg
            100                 105

<210> SEQ ID NO 25
<211> LENGTH: 106
<212> TYPE: PRT
<213> ORGANISM: Mus musculus
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (31)..(34)
<223> OTHER INFORMATION: Xaa can be any naturally occurring amino acid
<220> FEATURE:
<221> NAME/KEY: misc_feature
<222> LOCATION: (60)..(63)
<223> OTHER INFORMATION: Xaa can be any naturally occurring amino acid
<220> FEATURE:
<221> NAME/KEY: misc_feature
<222> LOCATION: (73)..(73)
<223> OTHER INFORMATION: Xaa can be any naturally occurring amino acid

<400> SEQUENCE: 25

```
Glu Phe Gln Leu Gln Gln Ser Gly Pro Xaa Glu Leu Val Lys Pro Gly
1               5                   10                  15

Ala Ser Val Lys Ile Ser Cys Lys Ala Ser Gly Tyr Ser Phe Xaa Xaa
            20                  25                  30

Xaa Xaa Thr Asp Tyr Asn Met Asn Trp Val Lys Gln Ser Asn Gly Lys
        35                  40                  45

Ser Leu Glu Trp Ile Gly Val Ile Asn Pro Asn Xaa Xaa Xaa Xaa Thr
50                  55                  60

Thr Ser Tyr Asn Gln Lys Phe Lys Xaa Gly Lys Ala Thr Leu Thr Val
65                  70                  75                  80

Asp Gln Ser Ser Ser Thr Ala Tyr Met Gln Leu Asn Ser Leu Thr Ser
                85                  90                  95

Ser Asp Ser Ala Val Tyr Tyr Cys Ala Arg
                100                 105

<210> SEQ ID NO 26
<211> LENGTH: 106
<212> TYPE: PRT
<213> ORGANISM: Homo sapiens
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (31)..(34)
<223> OTHER INFORMATION: Xaa can be any naturally occurring amino acid
<220> FEATURE:
<221> NAME/KEY: misc_feature
<222> LOCATION: (60)..(61)
<223> OTHER INFORMATION: Xaa can be any naturally occurring amino acid
<220> FEATURE:
<221> NAME/KEY: misc_feature
<222> LOCATION: (73)..(73)
<223> OTHER INFORMATION: Xaa can be any naturally occurring amino acid

<400> SEQUENCE: 26

Gln Val Gln Leu Val Gln Ser Gly Ala Xaa Glu Val Lys Lys Pro Gly
1               5                   10                  15

Ala Ser Val Lys Val Ser Cys Lys Ala Ser Gly Tyr Thr Phe Xaa Xaa
            20                  25                  30

Xaa Xaa Thr Gly Tyr Tyr Met His Trp Val Arg Gln Ala Pro Gly Gln
        35                  40                  45

Gly Leu Glu Trp Met Gly Trp Ile Asn Pro Asn Xaa Xaa Ser Gly Gly
50                  55                  60

Thr Asn Tyr Ala Gln Lys Phe Gln Xaa Gly Arg Val Thr Met Thr Arg
65                  70                  75                  80

Asp Thr Ser Ile Ser Thr Ala Tyr Met Glu Leu Ser Arg Leu Arg Ser
                85                  90                  95

Asp Asp Thr Ala Val Tyr Tyr Cys Ala Arg
                100                 105

<210> SEQ ID NO 27
<211> LENGTH: 106
<212> TYPE: PRT
<213> ORGANISM: Mus musculus
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (31)..(34)
<223> OTHER INFORMATION: Xaa can be any naturally occurring amino acid
```

```
<220> FEATURE:
<221> NAME/KEY: misc_feature
<222> LOCATION: (60)..(61)
<223> OTHER INFORMATION: Xaa can be any naturally occurring amino acid
<220> FEATURE:
<221> NAME/KEY: misc_feature
<222> LOCATION: (73)..(73)
<223> OTHER INFORMATION: Xaa can be any naturally occurring amino acid

<400> SEQUENCE: 27
```

Gln Val Gln Leu Gln Gln Pro Gly Ala Xaa Glu Leu Val Lys Pro Gly
1               5                   10                  15

Thr Ser Val Lys Leu Ser Cys Lys Ala Ser Gly Tyr Asn Phe Xaa Xaa
            20                  25                  30

Xaa Xaa Thr Asn Tyr Trp Ile Asn Trp Val Lys Leu Arg Pro Gly Gln
        35                  40                  45

Gly Leu Glu Trp Ile Gly Glu Ile Tyr Pro Gly Xaa Xaa Ser Gly Ser
    50                  55                  60

Thr Asn Tyr Asn Glu Lys Phe Lys Xaa Ser Lys Ala Thr Leu Thr Ala
65                  70                  75                  80

Asp Thr Ser Ser Ser Thr Ala Tyr Met Gln Leu Ser Ser Leu Ala Ser
            85                  90                  95

Glu Asp Ser Ala Leu Tyr Tyr Cys Ala Arg
            100                 105

```
<210> SEQ ID NO 28
<211> LENGTH: 106
<212> TYPE: PRT
<213> ORGANISM: Mus musculus
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (31)..(34)
<223> OTHER INFORMATION: Xaa can be any naturally occurring amino acid
<220> FEATURE:
<221> NAME/KEY: misc_feature
<222> LOCATION: (60)..(61)
<223> OTHER INFORMATION: Xaa can be any naturally occurring amino acid
<220> FEATURE:
<221> NAME/KEY: misc_feature
<222> LOCATION: (73)..(73)
<223> OTHER INFORMATION: Xaa can be any naturally occurring amino acid

<400> SEQUENCE: 28
```

Gln Val Gln Leu Gln Gln Pro Gly Ala Xaa Glu Leu Val Lys Pro Gly
1               5                   10                  15

Ala Ser Val Lys Met Ser Cys Lys Ala Ser Gly Tyr Thr Phe Xaa Xaa
            20                  25                  30

Xaa Xaa Thr Ser Tyr Trp Ile Thr Trp Val Lys Gln Arg Pro Gly Gln
        35                  40                  45

Gly Leu Glu Trp Ile Gly Asp Ile Tyr Pro Gly Xaa Xaa Ser Gly Ser
    50                  55                  60

Thr Asn Tyr Asn Glu Lys Phe Lys Xaa Ser Lys Ala Thr Leu Thr Val
65                  70                  75                  80

Asp Thr Ser Ser Ser Thr Ala Tyr Met Gln Leu Ser Ser Leu Thr Ser
            85                  90                  95

Glu Asp Ser Ala Val Tyr Tyr Cys Ala Arg
            100                 105

```
<210> SEQ ID NO 29
```

```
<211> LENGTH: 106
<212> TYPE: PRT
<213> ORGANISM: Homo sapiens
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (31)..(34)
<223> OTHER INFORMATION: Xaa can be any naturally occurring amino acid
<220> FEATURE:
<221> NAME/KEY: misc_feature
<222> LOCATION: (60)..(61)
<223> OTHER INFORMATION: Xaa can be any naturally occurring amino acid
<220> FEATURE:
<221> NAME/KEY: misc_feature
<222> LOCATION: (73)..(73)
<223> OTHER INFORMATION: Xaa can be any naturally occurring amino acid

<400> SEQUENCE: 29

Gln Val Gln Leu Val Gln Ser Gly Ala Xaa Glu Val Lys Lys Pro Gly
1               5                  10                  15

Ala Ser Val Lys Val Ser Cys Lys Ala Ser Gly Tyr Thr Phe Xaa Xaa
            20                  25                  30

Xaa Xaa Thr Ser Tyr Tyr Met His Trp Val Arg Gln Ala Pro Gly Gln
        35                  40                  45

Gly Leu Glu Trp Met Gly Ile Ile Asn Pro Ser Xaa Xaa Gly Gly Ser
    50                  55                  60

Thr Ser Tyr Ala Gln Lys Phe Gln Xaa Gly Arg Val Thr Met Thr Arg
65                  70                  75                  80

Asp Thr Ser Thr Ser Thr Val Tyr Met Glu Leu Ser Ser Leu Arg Ser
            85                  90                  95

Glu Asp Thr Ala Val Tyr Tyr Cys Ala Arg
            100                 105

<210> SEQ ID NO 30
<211> LENGTH: 106
<212> TYPE: PRT
<213> ORGANISM: Mus musculus
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (31)..(34)
<223> OTHER INFORMATION: Xaa can be any naturally occurring amino acid
<220> FEATURE:
<221> NAME/KEY: misc_feature
<222> LOCATION: (60)..(62)
<223> OTHER INFORMATION: Xaa can be any naturally occurring amino acid
<220> FEATURE:
<221> NAME/KEY: misc_feature
<222> LOCATION: (73)..(73)
<223> OTHER INFORMATION: Xaa can be any naturally occurring amino acid

<400> SEQUENCE: 30

Glu Val Lys Leu Val Glu Ser Gly Gly Xaa Gly Leu Val Lys Pro Gly
1               5                  10                  15

Gly Ser Leu Lys Leu Ser Cys Ala Ala Ser Gly Phe Thr Phe Xaa Xaa
            20                  25                  30

Xaa Xaa Ser Ser Tyr Ala Met Ser Trp Val Arg Gln Thr Pro Glu Lys
        35                  40                  45

Arg Leu Glu Trp Val Ala Ser Ile Ser Thr Gly Xaa Xaa Xaa Ala Ser
    50                  55                  60
```

```
Thr Tyr Phe Pro Asp Ser Val Lys Xaa Gly Arg Phe Thr Ile Ser Arg
 65                  70                  75                  80

Asp Asn Ala Arg Asn Ile Leu Tyr Leu Gln Met Ser Ser Leu Arg Ser
                 85                  90                  95

Glu Asp Thr Ala Met Tyr Tyr Cys Ala Arg
                100                 105

<210> SEQ ID NO 31
<211> LENGTH: 106
<212> TYPE: PRT
<213> ORGANISM: Mus musculus
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (31)..(34)
<223> OTHER INFORMATION: Xaa can be any naturally occurring amino acid
<220> FEATURE:
<221> NAME/KEY: misc_feature
<222> LOCATION: (60)..(61)
<223> OTHER INFORMATION: Xaa can be any naturally occurring amino acid
<220> FEATURE:
<221> NAME/KEY: misc_feature
<222> LOCATION: (73)..(73)
<223> OTHER INFORMATION: Xaa can be any naturally occurring amino acid

<400> SEQUENCE: 31

Glu Val Lys Leu Val Glu Ser Gly Gly Xaa Gly Leu Val Lys Pro Gly
  1               5                  10                  15

Gly Ser Leu Lys Leu Ser Cys Ala Ala Ser Gly Phe Ala Phe Xaa Xaa
                 20                  25                  30

Xaa Xaa Ser Ser Tyr Asp Met Ser Trp Val Arg Gln Thr Pro Glu Lys
             35                  40                  45

Arg Leu Glu Trp Val Ala Thr Ile Ser Ser Gly Xaa Xaa Gly Ala Ser
 50                  55                  60

Thr Tyr Tyr Pro Asp Ser Val Lys Xaa Gly Arg Phe Thr Ile Ser Arg
 65                  70                  75                  80

Asp Asn Ala Arg Asn Thr Leu Tyr Leu Gln Met Ser Ser Leu Arg Ser
                 85                  90                  95

Glu Asp Thr Ala Leu Tyr Tyr Cys Ala Arg
                100                 105

<210> SEQ ID NO 32
<211> LENGTH: 106
<212> TYPE: PRT
<213> ORGANISM: Homo sapiens
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (31)..(34)
<223> OTHER INFORMATION: Xaa can be any naturally occurring amino acid
<220> FEATURE:
<221> NAME/KEY: misc_feature
<222> LOCATION: (60)..(61)
<223> OTHER INFORMATION: Xaa can be any naturally occurring amino acid
<220> FEATURE:
<221> NAME/KEY: misc_feature
<222> LOCATION: (73)..(73)
<223> OTHER INFORMATION: Xaa can be any naturally occurring amino acid

<400> SEQUENCE: 32

Glu Val Gln Leu Val Glu Ser Gly Gly Xaa Gly Leu Val Gln Pro Gly
```

```
                1               5                  10                 15
Gly Ser Leu Arg Leu Ser Cys Ala Ala Ser Gly Phe Thr Phe Xaa Xaa
                20                 25                 30

Xaa Xaa Ser Ser Tyr Ala Met Ser Trp Val Arg Gln Ala Pro Gly Lys
            35                 40                 45

Gly Leu Glu Trp Val Ser Ala Ile Ser Gly Ser Xaa Xaa Gly Gly Ser
    50                 55                 60

Thr Tyr Tyr Ala Asp Ser Val Lys Xaa Gly Arg Phe Thr Ile Ser Arg
65                 70                 75                 80

Asp Asn Ser Lys Asn Thr Leu Tyr Leu Gln Met Asn Ser Leu Arg Ala
                85                 90                 95

Glu Asp Thr Ala Val Tyr Tyr Cys Ala Lys
            100                105
```

```
<210> SEQ ID NO 33
<211> LENGTH: 106
<212> TYPE: PRT
<213> ORGANISM: Mus musculus
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (31)..(34)
<223> OTHER INFORMATION: Xaa can be any naturally occurring amino acid
<220> FEATURE:
<221> NAME/KEY: misc_feature
<222> LOCATION: (60)..(62)
<223> OTHER INFORMATION: Xaa can be any naturally occurring amino acid
<220> FEATURE:
<221> NAME/KEY: misc_feature
<222> LOCATION: (73)..(73)
<223> OTHER INFORMATION: Xaa can be any naturally occurring amino acid

<400> SEQUENCE: 33

Gln Val Gln Leu Lys Glu Ser Gly Pro Xaa Gly Leu Val Ala Pro Ser
1               5                  10                 15

Gln Thr Leu Ser Ile Thr Cys Thr Val Ser Gly Phe Ser Leu Xaa Xaa
                20                 25                 30

Xaa Xaa Thr Ser Tyr Gly Val His Trp Val Arg Gln Pro Pro Gly Lys
            35                 40                 45

Gly Leu Glu Trp Leu Gly Val Ile Trp Ala Gly Xaa Xaa Xaa Gly Phe
    50                 55                 60

Thr Asn Tyr Asn Ser Ala Leu Lys Xaa Ser Arg Leu Ser Ile Ser Lys
65                 70                 75                 80

Asp Asn Ser Lys Ser Gln Val Leu Leu Lys Met Thr Ser Leu Gln Thr
                85                 90                 95

Asp Asp Thr Ala Met Tyr Tyr Cys Ala Arg
            100                105
```

```
<210> SEQ ID NO 34
<211> LENGTH: 106
<212> TYPE: PRT
<213> ORGANISM: Mus musculus
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (31)..(34)
<223> OTHER INFORMATION: Xaa can be any naturally occurring amino acid
<220> FEATURE:
```

```
<221> NAME/KEY: misc_feature
<222> LOCATION: (60)..(62)
<223> OTHER INFORMATION: Xaa can be any naturally occurring amino acid
<220> FEATURE:
<221> NAME/KEY: misc_feature
<222> LOCATION: (73)..(73)
<223> OTHER INFORMATION: Xaa can be any naturally occurring amino acid

<400> SEQUENCE: 34
```

Gln Val Gln Leu Lys Glu Ser Gly Pro Xaa Gly Leu Val Ala Pro Ser
1               5                   10                  15

Gln Ser Leu Ser Ile Thr Cys Thr Val Ser Gly Phe Ser Leu Xaa Xaa
            20                  25                  30

Xaa Xaa Thr Ser Tyr Gly Val His Trp Val Arg Gln Pro Pro Gly Lys
        35                  40                  45

Gly Leu Glu Trp Leu Gly Val Ile Trp Ala Gly Xaa Xaa Xaa Gly Ser
50                  55                  60

Thr Asn Tyr Asn Ser Ala Leu Met Xaa Ser Arg Leu Ser Ile Ser Lys
65                  70                  75                  80

Asp Asn Ser Lys Ser Gln Val Phe Leu Lys Met Asn Ser Leu Gln Thr
            85                  90                  95

Asp Asp Thr Ala Met Tyr Tyr Cys Ala Arg
            100                 105

```
<210> SEQ ID NO 35
<211> LENGTH: 106
<212> TYPE: PRT
<213> ORGANISM: Homo sapiens
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (31)..(34)
<223> OTHER INFORMATION: Xaa can be any naturally occurring amino acid
<220> FEATURE:
<221> NAME/KEY: misc_feature
<222> LOCATION: (60)..(62)
<223> OTHER INFORMATION: Xaa can be any naturally occurring amino acid
<220> FEATURE:
<221> NAME/KEY: misc_feature
<222> LOCATION: (73)..(73)
<223> OTHER INFORMATION: Xaa can be any naturally occurring amino acid

<400> SEQUENCE: 35
```

Gln Val Gln Leu Gln Glu Ser Gly Pro Xaa Gly Leu Val Lys Pro Ser
1               5                   10                  15

Gln Thr Leu Ser Leu Thr Cys Ala Val Tyr Gly Gly Ser Phe Xaa Xaa
            20                  25                  30

Xaa Xaa Ser Gly Tyr Tyr Trp Ser Trp Ile Arg Gln Pro Pro Gly Lys
        35                  40                  45

Gly Leu Glu Trp Ile Gly Glu Ile Asn His Ser Xaa Xaa Xaa Gly Ser
50                  55                  60

Thr Asn Tyr Asn Pro Ser Leu Lys Xaa Ser Arg Val Thr Ile Ser Val
65                  70                  75                  80

Asp Thr Ser Lys Asn Gln Phe Ser Leu Lys Leu Ser Ser Val Thr Ala
            85                  90                  95

Ala Asp Thr Ala Val Tyr Tyr Cys Ala Arg
            100                 105

```
<210> SEQ ID NO 36
<211> LENGTH: 406
```

```
<212> TYPE: PRT
<213> ORGANISM: Homo sapiens

<400> SEQUENCE: 36

Met His Arg Pro Arg Arg Arg Gly Thr Arg Pro Leu Leu Ala Leu
1               5                   10                  15

Leu Ala Ala Leu Leu Ala Ala Arg Gly Ala Ala Gln Glu Thr
            20                  25                  30

Glu Leu Ser Val Ser Ala Glu Leu Val Pro Thr Ser Ser Trp Asn Ile
            35                  40                  45

Ser Ser Glu Leu Asn Lys Asp Ser Tyr Leu Thr Leu Asp Glu Pro Met
        50                  55                  60

Asn Asn Ile Thr Thr Ser Leu Gly Gln Thr Ala Glu Leu His Cys Lys
65                  70                  75                  80

Val Ser Gly Asn Pro Pro Pro Thr Ile Arg Trp Phe Lys Asn Asp Ala
                85                  90                  95

Pro Val Val Gln Glu Pro Arg Arg Leu Ser Phe Arg Ser Thr Ile Tyr
            100                 105                 110

Gly Ser Arg Leu Arg Ile Arg Asn Leu Asp Thr Thr Asp Thr Gly Tyr
        115                 120                 125

Phe Gln Cys Val Ala Thr Asn Gly Lys Glu Val Val Ser Ser Thr Gly
    130                 135                 140

Val Leu Phe Val Lys Phe Gly Pro Pro Thr Ala Ser Pro Gly Tyr
145                 150                 155                 160

Ser Asp Glu Tyr Glu Glu Asp Gly Phe Cys Gln Pro Tyr Arg Gly Ile
                165                 170                 175

Ala Cys Ala Arg Phe Ile Gly Asn Arg Thr Val Tyr Met Glu Ser Leu
            180                 185                 190

His Met Gln Gly Glu Ile Glu Asn Gln Ile Thr Ala Ala Phe Thr Met
        195                 200                 205

Ile Gly Thr Ser Ser His Leu Ser Asp Lys Cys Ser Gln Phe Ala Ile
    210                 215                 220

Pro Ser Leu Cys His Tyr Ala Phe Pro Tyr Cys Asp Glu Thr Ser Ser
225                 230                 235                 240

Val Pro Lys Pro Arg Asp Leu Cys Arg Asp Glu Cys Glu Ile Leu Glu
                245                 250                 255

Asn Val Leu Cys Gln Thr Glu Tyr Ile Phe Ala Arg Ser Asn Pro Met
            260                 265                 270

Ile Leu Met Arg Leu Lys Leu Pro Asn Cys Glu Asp Leu Pro Gln Pro
        275                 280                 285

Glu Ser Pro Glu Ala Ala Asn Cys Ile Arg Ile Gly Ile Pro Met Ala
    290                 295                 300

Asp Pro Ile Asn Lys Asn His Lys Cys Tyr Asn Ser Thr Gly Val Asp
305                 310                 315                 320

Tyr Arg Gly Thr Val Ser Val Thr Lys Ser Gly Arg Gln Cys Gln Pro
                325                 330                 335

Trp Asn Ser Gln Tyr Pro His Thr His Thr Phe Thr Ala Leu Arg Phe
            340                 345                 350

Pro Glu Leu Asn Gly Gly His Ser Tyr Cys Arg Asn Pro Gly Asn Gln
        355                 360                 365

Lys Glu Ala Pro Trp Cys Phe Thr Leu Asp Glu Asn Phe Lys Ser Asp
    370                 375                 380

Leu Cys Asp Ile Pro Ala Cys Asp Ser Lys Asp Ser Lys Glu Lys Asn
385                 390                 395                 400
```

Lys Met Glu Ile Leu Tyr
                405

<210> SEQ ID NO 37
<211> LENGTH: 406
<212> TYPE: PRT
<213> ORGANISM: Mus musculus

<400> SEQUENCE: 37

Met His Arg Pro Arg Arg Gly Thr Arg Pro Pro Leu Ala Leu
1               5                   10                  15

Leu Ala Leu Leu Leu Ala Ala Arg Gly Ala Asp Ala Gln Glu Thr
            20                  25                  30

Glu Leu Ser Val Ser Ala Glu Leu Val Pro Thr Ser Ser Trp Asn Thr
            35                  40                  45

Ser Ser Glu Ile Asp Lys Gly Ser Tyr Leu Thr Leu Asp Glu Pro Met
        50                  55                  60

Asn Asn Ile Thr Thr Ser Leu Gly Gln Thr Ala Glu Leu His Cys Lys
65                  70                  75                  80

Val Ser Gly Asn Pro Pro Pro Ser Ile Arg Trp Phe Lys Asn Asp Ala
                85                  90                  95

Pro Val Val Gln Glu Pro Arg Arg Ile Ser Phe Arg Ala Thr Asn Tyr
            100                 105                 110

Gly Ser Arg Leu Arg Ile Arg Asn Leu Asp Thr Thr Asp Thr Gly Tyr
        115                 120                 125

Phe Gln Cys Val Ala Thr Asn Gly Lys Lys Val Val Ser Thr Thr Gly
    130                 135                 140

Val Leu Phe Val Lys Phe Gly Pro Pro Thr Ala Ser Pro Gly Ser
145                 150                 155                 160

Ser Asp Glu Tyr Glu Glu Asp Gly Phe Cys Gln Pro Tyr Arg Gly Ile
                165                 170                 175

Ala Cys Ala Arg Phe Ile Gly Asn Arg Thr Val Tyr Met Glu Ser Leu
            180                 185                 190

His Met Gln Gly Glu Ile Glu Asn Gln Ile Thr Ala Ala Phe Thr Met
        195                 200                 205

Ile Gly Thr Ser Ser His Leu Ser Asp Lys Cys Ser Gln Phe Ala Ile
    210                 215                 220

Pro Ser Leu Cys His Tyr Ala Phe Pro Tyr Cys Asp Glu Thr Ser Ser
225                 230                 235                 240

Val Pro Lys Pro Arg Asp Leu Cys Arg Asp Glu Cys Glu Val Leu Glu
                245                 250                 255

Asn Val Leu Cys Gln Thr Glu Tyr Ile Phe Ala Arg Ser Asn Pro Met
            260                 265                 270

Ile Leu Met Arg Leu Lys Leu Pro Asn Cys Glu Asp Leu Pro Gln Pro
        275                 280                 285

Glu Ser Pro Glu Ala Ala Asn Cys Ile Arg Ile Gly Ile Pro Met Ala
    290                 295                 300

Asp Pro Ile Asn Lys Asn His Lys Cys Tyr Asn Ser Thr Gly Val Asp
305                 310                 315                 320

Tyr Arg Gly Thr Val Ser Val Thr Lys Ser Gly Arg Gln Cys Gln Pro
                325                 330                 335

Trp Asn Ser Gln Tyr Pro His Ser His Thr Phe Thr Ala Leu Arg Phe
            340                 345                 350

Pro Glu Leu Asn Gly Gly His Ser Tyr Cys Arg Asn Pro Gly Asn Gln

```
             355                 360                 365
Lys Glu Ala Pro Trp Cys Phe Thr Leu Asp Glu Asn Phe Lys Ser Asp
        370                 375                 380

Leu Cys Asp Ile Pro Ala Cys Asp Ser Lys Asp Ser Lys Glu Lys Asn
385                 390                 395                 400

Lys Met Glu Ile Leu Tyr
                405
```